(12) United States Patent
Schulz-Trieglaff et al.

(10) Patent No.: US 12,217,832 B2
(45) Date of Patent: *Feb. 4, 2025

(54) DEEP LEARNING-BASED VARIANT CLASSIFIER

(71) Applicants: Illumina, Inc., San Diego, CA (US); Illumina Cambridge Limited, Cambridge (GB)

(72) Inventors: Ole Schulz-Trieglaff, Cambridge (GB); Anthony James Cox, Cambridge (GB); Kai-How Farh, San Mateo, CA (US)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/314,638

(22) Filed: May 9, 2023

(65) Prior Publication Data

US 2023/0386611 A1 Nov. 30, 2023

Related U.S. Application Data

(63) Continuation of application No. 16/247,487, filed on Jan. 14, 2019, now Pat. No. 11,705,219.

(Continued)

(51) Int. Cl.
*G16B 40/20* (2019.01)
*G06F 9/38* (2018.01)
(Continued)

(52) U.S. Cl.
CPC ........... *G16B 40/20* (2019.02); *G06F 9/3877* (2013.01); *G06F 18/2148* (2023.01);
(Continued)

(58) Field of Classification Search
CPC .... G06K 9/6257; G06K 9/628; G06F 9/3877; G06N 3/04; G06N 3/0454; G06N 3/084;
(Continued)

(56) References Cited

U.S. PATENT DOCUMENTS

| 5,641,658 | A | 6/1997 | Adams et al. |
|---|---|---|---|
| 7,057,026 | B2 | 6/2006 | Barnes et al. |

(Continued)

FOREIGN PATENT DOCUMENTS

| CA | 2894317 A1 | 12/2016 |
|---|---|---|
| CN | 102939304 A | 2/2013 |

(Continued)

OTHER PUBLICATIONS

Arik et al., Deep Voice: Real-time Neural Text-to-Speech, dated 2017, 17 pages.

(Continued)

*Primary Examiner* — Charles T Shedrick
(74) *Attorney, Agent, or Firm* — Keller Preece PLLC

(57) ABSTRACT

The technology disclosed directly operates on sequencing data and derives its own feature filters. It processes a plurality of aligned reads that span a target base position. It combines elegant encoding of the reads with a lightweight analysis to produce good recall and precision using lightweight hardware. For instance, one million training examples of target base variant sites with 50 to 100 reads each can be trained on a single GPU card in less than 10 hours with good recall and precision. A single GPU card is desirable because it a computer with a single GPU is inexpensive, almost universally within reach for users looking at genetic data. It is readily available on could-based platforms.

20 Claims, 16 Drawing Sheets

Related U.S. Application Data

(60) Provisional application No. 62/617,552, filed on Jan. 15, 2018.

(51) Int. Cl.
| | |
|---|---|
| G06F 18/214 | (2023.01) |
| G06F 18/2431 | (2023.01) |
| G06N 3/04 | (2023.01) |
| G06N 3/045 | (2023.01) |
| G06N 3/084 | (2023.01) |
| G16B 20/00 | (2019.01) |
| G16B 20/20 | (2019.01) |
| G16B 40/00 | (2019.01) |

(52) U.S. Cl.
CPC ........... *G06F 18/2431* (2023.01); *G06N 3/04* (2013.01); *G06N 3/045* (2023.01); *G06N 3/084* (2013.01); *G16B 20/00* (2019.02); *G16B 20/20* (2019.02); *G16B 40/00* (2019.02)

(58) Field of Classification Search
CPC ........ G16B 20/00; G16B 20/20; G16B 40/00; G16B 40/20
See application file for complete search history.

(56) References Cited

U.S. PATENT DOCUMENTS

| | | | |
|---|---|---|---|
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 9,115,353 | B2 | 8/2015 | Klausing et al. |
| 2002/0055100 | A1 | 5/2002 | Kawashima et al. |
| 2004/0002090 | A1 | 1/2004 | Mayer et al. |
| 2004/0096853 | A1 | 5/2004 | Mayer |
| 2007/0128624 | A1 | 6/2007 | Gormley et al. |
| 2007/0166705 | A1 | 7/2007 | Milton et al. |
| 2008/0009420 | A1 | 1/2008 | Schroth et al. |
| 2008/0108082 | A1 | 5/2008 | Rank et al. |
| 2008/0280773 | A1 | 11/2008 | Fedurco et al. |
| 2009/0088327 | A1 | 4/2009 | Rigatti et al. |
| 2011/0098193 | A1 | 4/2011 | Kingsmore et al. |
| 2013/0296175 | A1 | 11/2013 | Rafnar et al. |
| 2014/0143188 | A1 | 5/2014 | Mackey et al. |
| 2014/0280327 | A1 | 9/2014 | Pham et al. |
| 2014/0304270 | A1 | 10/2014 | Torkamani et al. |
| 2016/0085910 | A1 | 3/2016 | Bruand et al. |
| 2017/0286594 | A1 | 10/2017 | Reid et al. |
| 2017/0286830 | A1 | 10/2017 | El-Yaniv |
| 2018/0137406 | A1* | 5/2018 | Howard ............... G06N 3/0454 |
| 2018/0163261 | A1* | 6/2018 | Zeigler .................... C12Q 1/68 |
| 2019/0189242 | A1* | 6/2019 | Angiuoli ................ G16B 40/20 |
| 2019/0318806 | A1* | 10/2019 | Wise ....................... G16B 40/20 |
| 2020/0185055 | A1* | 6/2020 | Dubourg-Felonneau ................... G16B 30/10 |
| 2020/0194099 | A1* | 6/2020 | Li .......................... G16B 20/20 |
| 2020/0251183 | A1* | 8/2020 | Kashefhaghighi ..... G16B 40/20 |
| 2020/0302297 | A1* | 9/2020 | Jaganathan ........ G06V 10/7784 |

FOREIGN PATENT DOCUMENTS

| | | | |
|---|---|---|---|
| CN | 105934514 | A | 9/2016 |
| CN | 106459939 | A | 2/2017 |
| JP | 2017520821 | A | 12/2019 |
| JP | 2017033046 | A | 4/2020 |
| WO | 9106678 | A1 | 5/1991 |
| WO | 2004018497 | A2 | 3/2004 |
| WO | 2005068089 | A2 | 7/2005 |
| WO | 2007010252 | A1 | 1/2007 |
| WO | 2007123744 | A2 | 11/2007 |
| WO | 2008041002 | A2 | 4/2008 |
| WO | 2014142831 | A1 | 9/2014 |
| WO | 2016209999 | A1 | 12/2016 |
| WO | 2017017611 | A1 | 2/2017 |
| WO | 2017153556 | A1 | 9/2017 |
| WO | 2017214320 | A1 | 12/2017 |
| WO | 2018093780 | A1 | 5/2018 |
| WO | WO-2019140402 | A1 * | 7/2019 ........... G06F 9/3877 |
| WO | 2022155147 | A1 | 7/2022 |

OTHER PUBLICATIONS

Bentley et. al., Accurate Whole Human Genome Sequencing using Reversible Terminator Chemistry, Supplemental Information, Nature, dated Nov. 6, 2008, 55 pages, [retrieved on Jul. 21, 2021], retrieved from the internet URL: https://media.nature.com/original/nature-assets/nature/journal/v456/7218/extref/nature07517-s1.pdf.
Chen-et al_Rethinking-Atrous-Convolution-for-Semantic-Image-Segmentation _Dec. 5, 2017_14pgs.
Chin_Simple Convolutional Neural Network for Genomic Variant Calling with TensorFlow_2017_8pgs.
Chin_VariantNET_GitHub_Jan. 9, 2019_4pgs.
Ching-et al_Opportunities-and-obstacles-for-deep-learning-in-biology-and- medicine_May 28, 2017_102p.
Chollet_Xception: Deep-Learning-with-Depthwise-Separable-Convolutions_2017_8pgs.
Current-Challenges-In-Cardiovascular-Molecular-Diagnostics_2017_130pgs.pdf.
Dean-et al_Large-Scale-Distributed-Deep-Networks_Dec. 2012_11pgs.
DePristo et al., "DeepVariant: Highly Accurate Genomes With Deep Neural Networks," Google AI Blog, Dec. 4, 2017, 1 pages.
Dijke, "Convolutional Neural Networks for Regulatory Genomics", Jun. 17, 2017, Universiteit Leiden Opleiding Informatica, Master's Thesis, Leiden Institute of Advanced Computer Science (LIACS), Leiden University, The Netherlands, pp. 1-58.
Dong-et al_Comparison-and-integration-of-deleteriousness-prediction-methods-for-nonsynonymous-SNVS_Dec. 30, 2014_13pgs.
Dunn et al., Pisces: An Accurate and Versatile Variant Caller for Somatic and Germline Next-Generation Sequencing Data, dated Mar. 29, 2018, 3 pages.
Dunn Pisces Accurate and Versatile Variant Caller for Somatic Germline Next Generation Sequence Data_2018_3p.
Dunn-et al_Pisces-An-Accurate-and-Versatile-Single-Sample-Somatic-and-Germline-Variant-Caller_Aug. 20, 2017_1pg.
Friedman_Deep-learning-in-GATK4_Dec. 2017_11pgs.
GermlineEmpiricalVariantScore-EVS-Mode | Training_Illumina_GitHub_Jan. 12, 2018_6p.
GitHub_DeepVariant_Jan. 9, 2019_6pgs.
Goodfellow et al., Chapter 9—Convolutional Networks, Deep Learning, MIT Press, dated 2016, 41 pages.
Gu et. al., Recent Advances in Convolutional Neural Networks, dated Jan. 5, 2017, 37 pages.
He-et al_Deep-Residual-Learning-for-Image-Recognition_Dec. 10, 2015_12pgs.
Howard-et al_Mobilenets:Efficient-Convolutional-Neural-Networks-for-Mobile-Vision-Applications_Apr. 17, 2017_9pgs.
Huang et al., Densely Connected Convolutional Networks, dated Aug. 17, 2017, 9 pages.
Huang-et al_Speed-accuracy-trade-offs-for-modern-convolution_Apr. 25, 2017_10pgs.
Illumina_Complete-Secondary-Analysis-Workflow-for-the-Genome-Analyzer_Oct. 19, 2009_8pgs.
Illumina_Quality-Scores-for-Next-Generation-Sequencing_Oct. 31, 2011_2pgs.
Illumina_Understanding-Illumina-Quality-Scores_Apr. 23, 2014_2pgs.
Illumina, Nirvana Wiki, Github, 3 pages. Retrieved on Mar. 9, 2022. Retrieved from the internet [URL: https://github com/Illumina/Nirvana/wiki ].
Illumina Dragen Server Installation Guide, Document # 100000007500 v00, Jan. 2019, 21p.
Ioffe et al., Batch Normalization Accelerating Deep Network Training by Reducing Internal Covariate Shift, dated 2015 11 pages.

(56) References Cited

OTHER PUBLICATIONS

Kim-et al_Strelka2-Fast-and-accurate-variant-calling-for-clinical-sequencing-applications_Sep. 23, 2017_19pgs.
Kothen-Hill_Deep-Learning-Mutation-Prediction-Enable-EarlyStage-Lung-Cancer-Detect-Liquid-Biopsy_2018_24p.
Lin_Network-in-Network_Mar. 4, 2014_10Pgs.
Lizardi et al., Mutation detection and single-molecule counting using isothermal rolling-circle amplification, Nature Genetics, vol. 19, pp. 225-232, dated Jul. 1998.
Illumina, Pisces, Github, retrieved on Mar. 9, 2022, 5 pages. Retrieved from the internet [URL: https://github.com/ lumina/ Pisces .].
Methods for Strelka Small Variant Caller_Aug. 31, 2017_43pgs.
Molteni_Google-is-Giving-Away-AI-that-can-Build-Your-Genome-Sequence_Dec. 7, 2017_5pg.
O'Fallon et al,. A "support vector machine for identification of single-nucleotide polymorphisms from next-generation sequencing data," Bioinformatics 29, No. 11 (2013), p. 1361-1366.
Oord et al., WAVENET: A Generative Model for Raw Audio, dated Sep. 19, 2016, 15 pages.
Owano_DeepVariant-Tool-to-call-out-variants-in-sequencing-data-goes-open-source_Dec. 11, 2017_3p.
Piqueras, Autoregressive Model Based on a Deep Convolutional Neural Network for Audio Generation, Tampere University of Technology, dated 2016, 58 pages.
Poplin-et al_Creating-a-universal-SNP-and-small-indel-variant-caller-with-deep-neural-networks_Dec. 14, 2016_24pgs.pdf.
Qin-et al_FD-MobileNet-Improved-MobileNet-w-Fast-Downsampling-Strategy_Feb. 11, 2018_5pgs.
Rakocevic et al.. Fast and Accurate Genomic Analyses using Genome Graphs. biorxi. URL Inttps://www.biorxiv.org/Content/biorxiv/early/2018/03/20/194530.full.pdf], dated Mar. 20, 2018, 104 pages.
Running DeepVariant_Jan. 9, 2019_18pgs.
Sandler-etal_MobileNetV2-Inverted-Residuals-and-Linear-Bottlenecks_Apr. 2, 2018_14pgs.
Saunders_Strelk accurate somatic small variant calling from sequenced tumor normal sample pairs_2012_7p.
Saunders-etal_Supplementary-Methods-for-Strelka-Accurate-somatic-small-variant-calling_Mar. 28, 2012_4p.
Shlens_Train-your-own-image-classifier-with-Inception-in-TensorFlow_Mar. 9, 2016-4p.
Sifre_analysis-and-interpretation-of-single-nucleotide-variation-in-human-disease_2012_12pgs.
Sifre_Rigid-motion-Scattering-for-Image-Classification_Oct. 6, 2014_128pgs.
Sifre_Rotation-Scaling-Deformation-Invariant-Scattering-for-Texture-Discrimination_2013_8pgs.
Spinella_SNooPerMachineLearningBasedMethodSomaticVariantId FromLlowpassNextGenSequencing_2016.
Srivastava_Dropout A Simple Way to Prevent Neural Networks fromOverfitting_2014_30p.
Srivastava et al., Highway Networks, dated 2015, 6 pages.
Strelka2_germline-and-somatic-small-variant-callerIllumina_GitHub_Jan. 10, 2019_3p.
StrelkaUserGuide_Illumina_GitHub_Jan. 12, 2018_10p.
Strom_Current-practices-and-guidelines-for-clinical-next-generation-sequencing-oncology-testing_Jan. 2, 2016-9gs.pdf.
Stromberb-et al_Clinical-grade-variant-annotation_5pgs.
Stromberg-etal_Nirvana-Clinical-Grade-Variant-Annotator_Aug. 20, 2017_1p.
SupplementaryNotesForStrelka2_13p.
Szegedy_Rethinking-the-Inception-Architecture-for-Computer-Vision_Dec. 11, 2015_10pgs.
Szegedy-et al_Going-deeper-with-convolutions_2015_9pgs.
Szegedy-etal_Inception-v4-Inception-ResNet-and-the-Impact-of-Residual-Connections-on-_earning Feb. 23, 2016 12pgs.
Takata_ExomeSequencIdentifiesNovelMissenseVariantRRM2BAssociatedWOphthalmoplegia_2011_7pgs.
Torracinta_AdaptiveSomaticMutationsCallsWithDeepLearningand SemiSimulatedData_Oct. 4, 2016_13p.
Wolterink et al., Dilated Convolutional Neural Networks for Cardiovascular MR Segmentation in Congenital Heart Disease, dated 2017, 9pages.
Wu, Introduction to Convolutional Neural Networks, Nanjing University, dated 2017, 31 pages.
Xie-etal_Aggregated-Residual-Transformations-for-Deep-Neural-Networks_Apr. 11, 2017_10pgs.
Xiong et al., "The human splicing code reveals new insights into the genetic determinants of disease," Science 347, ho. 6218 (2015), 1254806, 10 pages.
Yu et al., Multi-Scale Context Aggregation by Dilated Convolutions, ICLR 2016, dated Apr. 30, 2016, 13 pages.
Zhang et al., "DeepSplice: Deep classification of novel splice junctions revealed by RNA-seq." nl 2016 IEEE international conference on bioinformatics and biomedicine (BIBM), pp. 330-333. IEEE, 2016.
Zhang_Google-Taught-an-AI-That-Sorts-Cat-Photos-to-Analyze-DNA_Dec. 7, 2017_6pgs.
Zhang_ShuffleNetAn-Extremely-Efficient-Convolutional-Neural-Network-for-Mobile-Devices_Dec. 7, 2017_9p.
Ryan Poplin et al., "Creating a universal SNP and small indel variant caller with deep neural networks", bioRxiv, [online], May 17, 2017, [retrieved on May 23, 2024], Internet <URL: https://web.archive.org/web/20170517065414/https://www.biorxiv.org/content/biorxiv/early/2016/12/14/092890.full.pdf>.

* cited by examiner

Variant Classifier CNN Architecture 300B

- 220x100x10 Input comprising the following channels:
  - One-hot encode ACGT of the read (4 bits)
  - One-hot encode ACGT of the reference (4 bits)
  - Quality score (1 bit)
  - Strand (1 bit)
- CONV 5x5 and Maxpool (2:1, 2:1) → 108x48x32
- CONV 5x5 and Maxpool (2:1, 2:1) → 52x22x32
- CONV 5x5 and Maxpool (2:1, 2:1) → 25x9x32
- CONV 5x5, no Maxpool → 20x5x32
- CONV 5x5, no Maxpool → 16x1x32
- CONV 5x5, no Maxpool → 11x1x32
- CONV 5x5, no Maxpool → 7x1x32
- → Flatten to 224 Units + Concatenate 23 EVS Features → 247 Units
- Fully-Connected 256 Units
- → Output

FIG. 3B

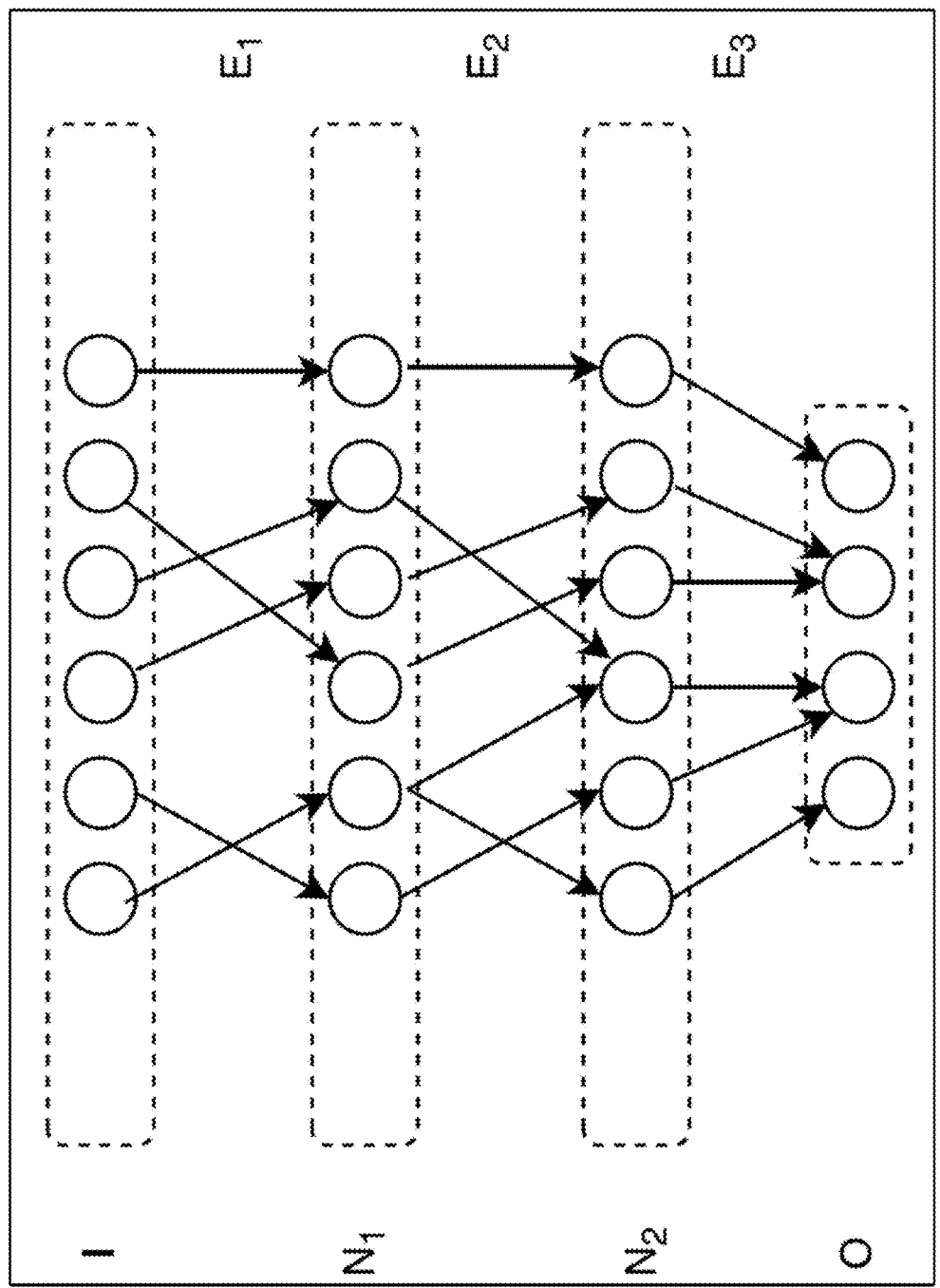

DEEP LEARNING-BASED VARIANT CLASSIFIER

PRIORITY APPLICATION

This application is a continuation of U.S. patent application Ser. No. 16/247,487, entitled "Deep Learning-Based Variant Classifier," which claims priority to or the benefit of U.S. Provisional Patent Application No. 62/617,552, entitled "DEEP LEARNING-BASED VARIANT CLASSIFIER," filed on Jan. 15, 2018. The priority application is hereby incorporated by reference for all purposes.

INCORPORATIONS

The following are incorporated by reference for all purposes as if fully set forth herein:

Strelka™ application by Illumina Inc. hosted at https://github.com/Illumina/strelka and described in the article T Saunders, Christopher & Wong, Wendy & Swamy, Sajani & Becq, Jennifer & J Murray, Lisa & Cheetham, Keira. (2012). Strelka: Accurate somatic small-variant calling from sequenced tumor-normal sample pairs. Bioinformatics (Oxford, England). 28. 1811-7;

Strelka2™ application by Illumina Inc. hosted at https://github.com/Illumina/strelka and described in the article Kim, S., Scheffler, K., Halpern, A. L., Bekritsky, M. A., Noh, E., Milberg, M., Chen, X., Beyter, D., Krusche, P., and Saunders, C. T. (2017);

A. van den Oord, S. Dieleman, H. Zen, K. Simonyan, O. Vinyals, A. Graves, N. Kalchbrenner, A. Senior, and K. Kavukcuoglu, "WAVENET: A GENERATIVE MODEL FOR RAW AUDIO," arXiv:1609.03499, 2016;

S. Ö. Arik, M. Chrzanowski, A. Coates, G. Diamos, A. Gibiansky, Y. Kang, X. Li, J. Miller, A. Ng, J. Raiman, S. Sengupta and M. Shoeybi, "DEEP VOICE: REAL-TIME NEURAL TEXT-TO-SPEECH," arXiv:1702.07825, 2017;

F. Yu and V. Koltun, "MULTI-SCALE CONTEXT AGGREGATION BY DILATED CONVOLUTIONS," arXiv:1511.07122, 2016;

K. He, X. Zhang, S. Ren, and J. Sun, "DEEP RESIDUAL LEARNING FOR IMAGE RECOGNITION," arXiv:1512.03385, 2015;

R. K. Srivastava, K. Greff, and J. Schmidhuber, "HIGHWAY NETWORKS," arXiv: 1505.00387, 2015;

G. Huang, Z. Liu, L. van der Maaten and K. Q. Weinberger, "DENSELY CONNECTED CONVOLUTIONAL NETWORKS," arXiv:1608.06993, 2017;

C. Szegedy, W. Liu, Y. Jia, P. Sermanet, S. Reed, D. Anguelov, D. Erhan, V. Vanhoucke, and A. Rabinovich, "GOING DEEPER WITH CONVOLUTIONS," arXiv:1409.4842, 2014;

S. Ioffe and C. Szegedy, "BATCH NORMALIZATION: ACCELERATING DEEP NETWORK TRAINING BY REDUCING INTERNAL COVARIATE SHIFT," arXiv:1502.03167, 2015;

Srivastava, Nitish, Hinton, Geoffrey, Krizhevsky, Alex, Sutskever, Ilya, and Salakhutdinov, Ruslan, "DROPOUT: A SIMPLE WAY TO PREVENT NEURAL NETWORKS FROM OVERFITTING," The Journal of Machine Learning Research, 15 (1):1929-1958, 2014;

J. M. Wolterink, T. Leiner, M. A. Viergever, and I. Iggum, "DILATED CONVOLUTIONAL NEURAL NETWORKS FOR CARDIOVASCULAR MR SEGMENTATION IN CONGENITAL HEART DISEASE," arXiv:1704.03669, 2017;

L. C. Piqueras, "AUTOREGRESSIVE MODEL BASED ON A DEEP CONVOLUTIONAL NEURAL NETWORK FOR AUDIO GENERATION," Tampere University of Technology, 2016;

J. Wu, "Introduction to Convolutional Neural Networks," Nanjing University, 2017;

I. J. Goodfellow, D. Warde-Farley, M. Mirza, A. Courville, and Y. Bengio, "CONVOLUTIONAL NETWORKS", Deep Learning, MIT Press, 2016;

J. Gu, Z. Wang, J. Kuen, L. Ma, A. Shahroudy, B. Shuai, T. Liu, X. Wang, and G. Wang, "RECENT ADVANCES IN CONVOLUTIONAL NEURAL NETWORKS," arXiv: 1512.07108, 2017;

M. Lin, Q. Chen, and S. Yan, "Network in Network," in Proc. of ICLR, 2014;

L. Sifre, "Rigid-motion Scattering for Image Classification, Ph.D. thesis, 2014;

L. Sifre and S. Mallat, "Rotation, Scaling and Deformation Invariant Scattering for Texture Discrimination," in Proc. of CVPR, 2013;

F. Chollet, "Xception: Deep Learning with Depthwise Separable Convolutions," in Proc. of CVPR, 2017;

X. Zhang, X. Zhou, M. Lin, and J. Sun, "ShuffleNet: An Extremely Efficient Convolutional Neural Network for Mobile Devices," in arXiv:1707.01083, 2017;

K. He, X. Zhang, S. Ren, and J. Sun, "Deep Residual Learning for Image Recognition," in Proc. of CVPR, 2016;

S. Xie, R. Girshick, P. Dollár, Z. Tu, and K. He, "Aggregated Residual Transformations for Deep Neural Networks," in Proc. of CVPR, 2017;

A. G. Howard, M. Zhu, B. Chen, D. Kalenichenko, W. Wang, T. Weyand, M. Andreetto, and H. Adam, "Mobilenets: Efficient Convolutional Neural Networks for Mobile Vision Applications," in arXiv:1704.04861, 2017;

M. Sandler, A. Howard, M. Zhu, A. Zhmoginov, and L. Chen, "MobileNetV2: Inverted Residuals and Linear Bottlenecks," in arXiv:1801.04381v3, 2018;

Z. Qin, Z. Zhang, X. Chen, and Y. Peng, "FD-MobileNet: Improved MobileNet with a Fast Downsampling Strategy," in arXiv:1802.03750, 2018;

PCT International Patent Application No. PCT/US17/61554, titled "Validation Methods and Systems for Sequence Variant Calls", filed on Nov. 14, 2017;

U.S. Provisional Patent Application No. 62/447,076, titled "Validation Methods and Systems for Sequence Variant Calls", filed on Jan. 17, 2017;

U.S. Provisional Patent Application No. 62/422,841, titled "Methods and Systems to Improve Accuracy in Variant Calling", filed on Nov. 16, 2016; and N. ten DIJKE, "Convolutional Neural Networks for Regulatory Genomics," Master's Thesis, Universiteit Leiden Opleiding Informatica, 17 Jun. 2017.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep learning and convolutional neural networks (CNNs) for analyzing ordered data.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Accurate identification of variant in genetic sequences has many important impacts and has garnered significant attention. The latest effort to apply Google's Inception engine to variant calling is interesting, but extremely resource intensive. A more efficient approach is needed.

Next-generation sequencing has made large amounts of sequenced data available for variant classification. Sequenced data are highly correlated and have complex interdependencies, which has hindered the application of traditional classifiers like support vector machine to the variant classification task. Advanced classifiers that are capable of extracting high-level features from sequenced data are thus desired.

Deep neural networks are a type of artificial neural networks that use multiple nonlinear and complex transforming layers to successively model high-level features and provide feedback via backpropagation. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks and recurrent neural networks are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. A hallmark of convolutional neural networks is the use of convolution filters. Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, an opportunity arises to use deep neural networks for variant classification.

BRIEF DESCRIPTION OF THE DRAWINGS

FIG. 3B illustrates another implementation of the architecture of the convolutional neural network of the variant classifier of FIG. 1A.

FIG. 4A depicts a fully-connected (FC) network.

DETAILED DESCRIPTION

Figure 1:
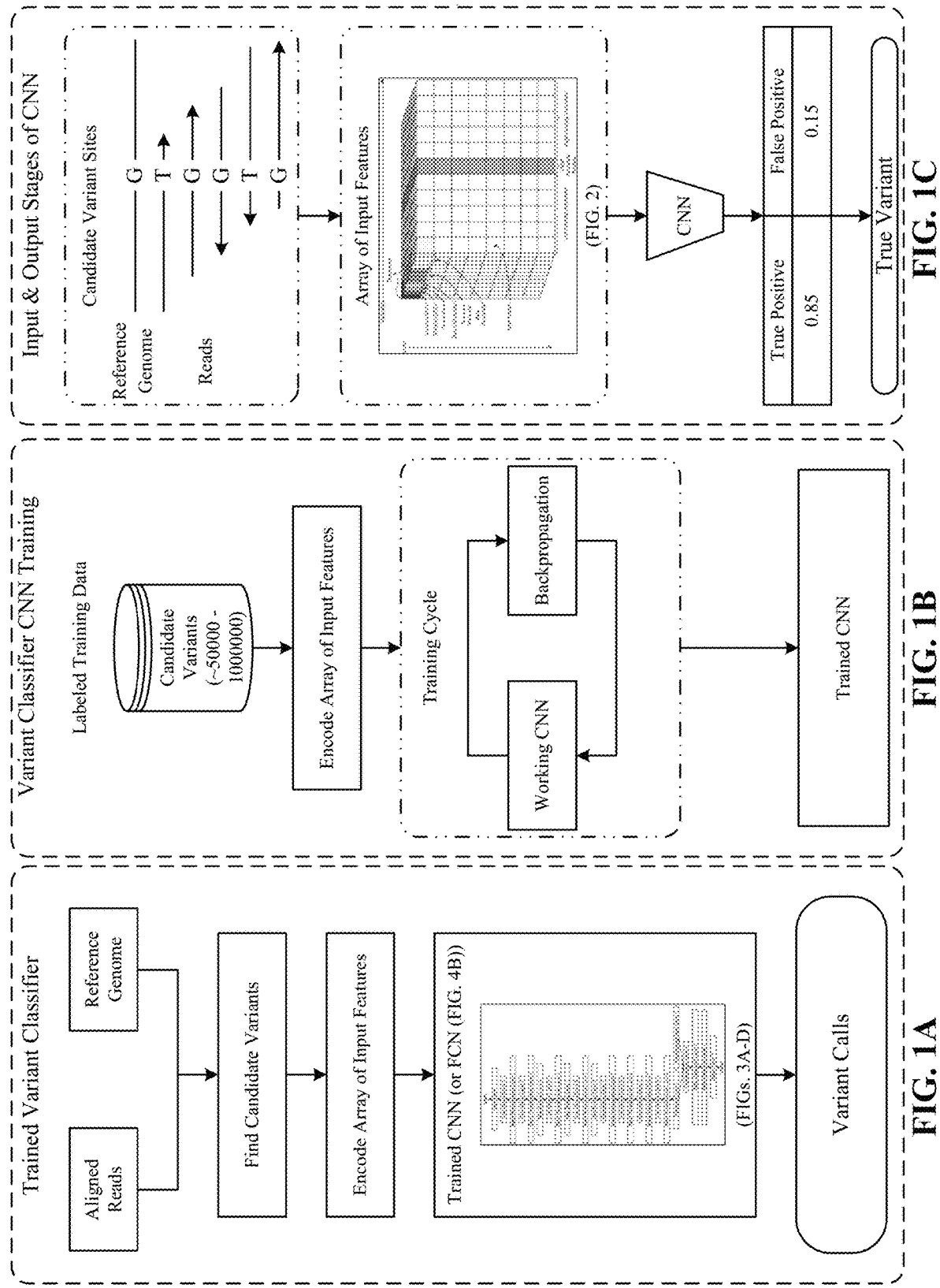
FIG. 1A shows one implementation of variant calling by a trained variant classifier disclosed herein. The trained variant classifier includes a convolutional neural network (CNN).
FIG. 1B illustrates one implementation of training the variant classifier of FIG. 1A using labeled training data comprising candidate variants.
FIG. 1C depicts one implementation of input and output modules of convolutional neural network processing of the variant classifier of FIG. 1A.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Introduction

The technology disclosed directly operates on DNA sequencing data and derives its own feature filters. It processes plurality of aligned reads (e.g., read depth ranging from 10 to 500) that span a target base position. It combines elegant encoding of the reads with a lightweight analysis to produce good recall and precision using lightweight hardware. For instance, one million training examples of target base variant sites with 50 to 100 reads each can be trained on a single GPU card in less than 10 hours with good recall and precision. A single GPU card is desirable because it a computer with a single GPU is inexpensive, almost universally within reach for users looking at genetic data. It is readily available on could-based platforms.

Elegant encoding combines the following data for reads centered on a target base, flanked on each side by 110 bases or more. Of course, few, if any reads will span the 221 base sequence, so most reads will have null bases on one or both ends of the read sequence. The data encoded for each base in a read sequence includes the individual read, a corresponding reference base from a reference read, a base call accuracy score from reading the base, a deoxyribonucleic acid (abbreviated DNA) strandedness of reading the base, an insertion count of insertion changes adjoining the base, and deletion flag to indicate that alignment determined that the read had a deletion at the individual read site.

In this encoding, insertions and deletions are handled differently. Between the positions of any two reads there can be an arbitrary number of insertions. The count of his number of insertions is used to represent an arbitrary number between reference positions. The calls of the inserted bases are not used, because misalignment among reads would result. Deletions take place at a particular position that can be flagged. If there are multiple deletions between two individual reads, after alignment, multiple deletion flags can be set at the deletion sites. A deleted base should not be assigned an ACGT code, as none applies.

This is a simple encoding system, not involving translation into a color space or adaption for processing by an image handling engine such as Inception. Simplicity contributes to fast training.

When more computing resources are available, sequences longer than 221 base positions can be used. As platforms evolve to produce longer read sequence, advantages of using more flanking bases are expected to become apparent.

The per-read data above can be supplemented by per-variant characterization data generated by a legacy system, during training and optionally during operation. There are many rule-based, hand-crafted systems that characterize variants at specific positions. One or more inputs, per-variant, can be used as inputs after processing the multiple reads through convolutional layers. The late added, per-variant input shortens training. This is expected, because the accuracy of legacy systems is already high, estimated in excess of 90 percent.

The lightweight analysis structure also contributes to fast training. In some embodiments, five convolutional layers for processing the per-read data, followed by a two layer fully connected structure that accepts input from the convolutional output and from the per-variant data has proven to be a lightweight and accurate network structure. Success also has been achieved with seven and eight convolutional layers, so two to eight layers work and more layers could be used.

In more detail, the first convolutional layer accepts the listed encoding in a 221 (base) by 100 (reads) by 12 (attributes, with one-hot encoding of ACGT reads). The center base is taken as the target position. A number of randomly initialized or previously trained filters are applied. In one design, 32 convolution filters are used at a layer. Multi-dimensional filters tend to collapse rows.

With a million training and verification samples available, seven training epochs has given good results. The number of training epochs should be limited to avoid overfitting. Limiting the number of epochs can be combined with dropouts to avoid overfitting.

Terminology

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

As used herein, the following terms have the meanings indicated.

A base refers to a nucleotide base or nucleotide, A (adenine), C (cytosine), T (thymine), or G (guanine). This application uses "base(s)" and "nucleotide(s)" interchangeably.

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some implementations, a site may be a residue, a sequence tag, or a segment's position on a sequence. The term "locus" may be used to refer to the specific location of a nucleic acid sequence or polymorphism on a reference chromosome.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects. The application uses "read(s)" and "sequence read(s)" interchangeably.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. In one example, a series of operations may be performed as follows; (a) generate clusters of nucleic acids; (b) linearize the nucleic acids; (c) hybridize a first sequencing primer and carry out repeated cycles of extension, scanning and deblocking, as set forth above; (d) "invert" the target nucleic acids on the flow cell surface by synthesizing a complimentary copy; (e) linearize the resynthesized strand; and (f) hybridize a second sequencing primer and carry out repeated cycles of extension, scanning and deblocking, as set forth above. The inversion operation can be carried out be delivering reagents as set forth above for a single cycle of bridge amplification.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the noncoding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about 107 times larger. In one example, the reference genome sequence is that of a full length human genome. In another example, the reference genome sequence is limited to a specific human chromosome such as chromosome 13. In some implementations, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various implementations, the reference genome is a consensus sequence or other combination derived from multiple individuals. However, in certain applications, the reference sequence may be taken from a particular individual. In other implementations, the "genome" also covers so-called "graph genomes", which use a particular storage format and representation of the genome sequence. In one implementation, graph genomes store data in a linear file. In another implementation, the graph genomes refer to a representation where alternative sequences (e.g., different copies of a chromosome with small differences) are stored as different paths in a graph. Additional information regarding graph genome implementations can be found in https://www.biorxiv.org/content/biorxiv/early/2018/03/20/194530.full.pdf, the content of which is hereby incorporated herein by reference in its entirety.

The term "read" refer to a collection of sequence data that describes a fragment of a nucleotide sample or reference. The term "read" may refer to a sample read and/or a reference read. Typically, though not necessarily, a read represents a short sequence of contiguous base pairs in the sample or reference. The read may be represented symbolically by the base pair sequence (in ATCG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each read may vary from about 30 bp to more than 10,000 bp. For example, the DNA sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain implementations, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain implementations, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "mapping", "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain implementations, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The term "variant" refers to a nucleic acid sequence that is different from a nucleic acid reference. Typical nucleic acid sequence variant includes without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base. A variant that is to be classified as somatic or germline by the variant classifier is also referred to herein as the "variant under test".

The term "noise" refers to a mistaken variant call resulting from one or more errors in the sequencing process and/or in the variant call application.

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The term "variant allele frequency (VAF)" refers to the percentage of sequenced reads observed matching the variant divided by the overall coverage at the target position. VAF is a measure of the proportion of sequenced reads carrying the variant.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some implementations, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more implementations may use count scores when analyzing the data. A count score may be based on number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some implementations, the count score may be a value that is equal to the read count. In other implementations, the count score may be based on the read count and other information. For example, a count score may be based on the read count for a particular allele of a genetic locus and a total number of reads for the genetic locus. In some implementations, the count score may be based on the read count and previously-obtained data for the genetic locus. In some implementations, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele.

The terms "coverage" or "fragment coverage" refer to a count or other measure of a number of sample reads for the same fragment of a sequence. A read count may represent a count of the number of reads that cover a corresponding fragment. Alternatively, the coverage may be determined by multiplying the read count by a designated factor that is based on historical knowledge, knowledge of the sample, knowledge of the locus, etc.

The term "read depth" (conventionally a number followed by "x") refers to the number of sequenced reads with overlapping alignment at the target position. This is often expressed as an average or percentage exceeding a cutoff over a set of intervals (such as exons, genes, or panels). For example, a clinical report might say that a panel average coverage is 1,105× with 98% of targeted bases covered >100×.

The terms "base call quality score" or "Q score" refer to a PHRED-scaled probability ranging from 0-50 inversely proportional to the probability that a single sequenced base is correct. For example, a T base call with Q of 20 is considered likely correct with a probability of 99.99%. Any base call with Q<20 should be considered low quality, and any variant identified where a substantial proportion of sequenced reads supporting the variant are of low quality should be considered potentially false positive.

The terms "variant reads" or "variant read number" refer to the number of sequenced reads supporting the presence of the variant.

Regarding "strandedness" (or DNA strandedness), the genetic message in DNA can be represented as a string of the letters A, G, C, and T. For example, 5'-AGGACA-3'. Often, the sequence is written in the direction shown here, i.e., with the 5' end to the left and the 3' end to the right. DNA may sometimes occur as single-stranded molecule (as in certain viruses), but normally we find DNA as a double-stranded unit. It has a double helical structure with two antiparallel strands. In this case, the word "antiparallel" means that the two strands run in parallel, but have opposite polarity. The double-stranded DNA is held together by pairing between bases and the pairing is always such that adenine (A) pairs with thymine (T) and cytosine (C) pairs with guanine (G). This pairing is referred to as complementarity, and one strand of DNA is said to be the complement of the other. The double-stranded DNA may thus be represented as two strings, like this: 5'-AGGACA-3' and 3'-TCCTGT-5'. Note that the two strands have opposite polarity. Accordingly, the strandedness of the two DNA strands can be referred to as the reference strand and its complement, forward and reverse strands, top and bottom strands, sense and antisense strands, or Watson and Crick strands.

The reads alignment (also called reads mapping) is the process of figuring out where in the genome a sequence is from. Once the alignment is performed, the "mapping quality" or the "mapping quality score (MAPQ)" of a given read quantifies the probability that its position on the genome is correct. The mapping quality is encoded in the phred scale where P is the probability that the alignment is not correct. The probability is calculated as: $P=10^{(-MAPQ/10)}$, where MAPQ is the mapping quality. For example, a mapping quality of 40=10 to the power of −4, meaning that there is a 0.01% chance that the read was aligned incorrectly. The mapping quality is therefore associated with several alignment factors, such as the base quality of the read, the complexity of the reference genome, and the paired-end information. Regarding the first, if the base quality of the read is low, it means that the observed sequence might be wrong and thus its alignment is wrong. Regarding the second, the mappability refers to the complexity of the genome. Repeated regions are more difficult to map and reads falling in these regions usually get low mapping quality. In this context, the MAPQ reflects the fact that the reads are not uniquely aligned and that their real origin cannot be determined. Regarding the third, in case of paired-end sequencing data, concordant pairs are more likely to be well aligned. The higher is the mapping quality, the better is the alignment. A read aligned with a good mapping quality usually means that the read sequence was good and was aligned with few mismatches in a high mappability region. The MAPQ value can be used as a quality control of the alignment results. The proportion of reads aligned with an MAPQ higher than 20 is usually for downstream analysis.

Sequencing Process

Implementations set forth herein may be applicable to analyzing nucleic acid sequences to identify sequence variations. Implementations may be used to analyze potential variants/alleles of a genetic position/locus and determine a genotype of the genetic locus or, in other words, provide a genotype call for the locus. By way of example, nucleic acid sequences may be analyzed in accordance with the methods and systems described in US Patent Application Publication No. 2016/0085910 and US Patent Application Publication No. 2013/0296175, the complete subject matter of which are expressly incorporated by reference herein in their entirety.

In one implementation, a sequencing process includes receiving a sample that includes or is suspected of including nucleic acids, such as DNA. The sample may be from a known or unknown source, such as an animal (e.g., human), plant, bacteria, or fungus. The sample may be taken directly from the source. For instance, blood or saliva may be taken directly from an individual. Alternatively, the sample may not be obtained directly from the source. Then, one or more processors direct the system to prepare the sample for sequencing. The preparation may include removing extraneous material and/or isolating certain material (e.g., DNA). The biological sample may be prepared to include features for a particular assay. For example, the biological sample may be prepared for sequencing-by-synthesis (SBS). In certain implementations, the preparing may include amplification of certain regions of a genome. For instance, the preparing may include amplifying predetermined genetic loci that are known to include STRs and/or SNPs. The genetic loci may be amplified using predetermined primer sequences.

Next, the one or more processors direct the system to sequence the sample. The sequencing may be performed through a variety of known sequencing protocols. In particular implementations, the sequencing includes SBS. In SBS, a plurality of fluorescently-labeled nucleotides are used to sequence a plurality of clusters of amplified DNA (possibly millions of clusters) present on the surface of an optical substrate (e.g., a surface that at least partially defines a channel in a flow cell). The flow cells may contain nucleic acid samples for sequencing where the flow cells are placed within the appropriate flow cell holders.

The nucleic acids can be prepared such that they comprise a known primer sequence that is adjacent to an unknown target sequence. To initiate the first SBS sequencing cycle, one or more differently labeled nucleotides, and DNA polymerase, etc., can be flowed into/through the flow cell by a fluid flow subsystem. Either a single type of nucleotide can be added at a time, or the nucleotides used in the sequencing procedure can be specially designed to possess a reversible termination property, thus allowing each cycle of the sequencing reaction to occur simultaneously in the presence of several types of labeled nucleotides (e.g., A, C, T, G). The nucleotides can include detectable label moieties such as fluorophores. Where the four nucleotides are mixed together, the polymerase is able to select the correct base to incorporate and each sequence is extended by a single base. Non-incorporated nucleotides can be washed away by flowing a wash solution through the flow cell. One or more lasers may excite the nucleic acids and induce fluorescence. The fluorescence emitted from the nucleic acids is based upon the fluorophores of the incorporated base, and different fluorophores may emit different wavelengths of emission light. A deblocking reagent can be added to the flow cell to remove reversible terminator groups from the DNA strands that were extended and detected. The deblocking reagent can then be washed away by flowing a wash solution through the flow cell. The flow cell is then ready for a further cycle of sequencing starting with introduction of a labeled nucleotide as set forth above. The fluidic and detection operations can be repeated several times to complete a sequencing run. Example sequencing methods are described, for example, in Bentley et al., Nature 456:53-59 (2008), International Publication No. WO 04/018497; U.S. Pat. No. 7,057,026; International Publication No. WO 91/06678; International Publication No. WO 07/123744; U.S. Pat. Nos. 7,329,492; 7,211,414; 7,315,019; 7,405,281, and U.S. Patent Application Publication No. 2008/0108082, each of which is incorporated herein by reference.

In some implementations, nucleic acids can be attached to a surface and amplified prior to or during sequencing. For example, amplification can be carried out using bridge amplification to form nucleic acid clusters on a surface. Useful bridge amplification methods are described, for example, in U.S. Pat. No. 5,641,658; U.S. Patent Application Publication No. 2002/0055100; U.S. Pat. No. 7,115,400; U.S. Patent Application Publication No. 2004/0096853; U.S. Patent Application Publication No. 2004/0002090; U.S. Patent Application Publication No. 2007/0128624; and U.S. Patent Application Publication No. 2008/0009420, each of which is incorporated herein by reference in its entirety. Another useful method for amplifying nucleic acids on a surface is rolling circle amplification (RCA), for example, as described in Lizardi et al., Nat. Genet. 19:225-232 (1998)

and U.S. Patent Application Publication No. 2007/0099208 A1, each of which is incorporated herein by reference.

One example SBS protocol exploits modified nucleotides having removable 3' blocks, for example, as described in International Publication No. WO 04/018497, U.S. Patent Application Publication No. 2007/0166705A1, and U.S. Pat. No. 7,057,026, each of which is incorporated herein by reference. For example, repeated cycles of SBS reagents can be delivered to a flow cell having target nucleic acids attached thereto, for example, as a result of the bridge amplification protocol. The nucleic acid clusters can be converted to single stranded form using a linearization solution. The linearization solution can contain, for example, a restriction endonuclease capable of cleaving one strand of each cluster. Other methods of cleavage can be used as an alternative to restriction enzymes or nicking enzymes, including inter alia chemical cleavage (e.g., cleavage of a diol linkage with periodate), cleavage of abasic sites by cleavage with endonuclease (for example 'USER', as supplied by NEB, Ipswich, Mass., USA, part number M5505S), by exposure to heat or alkali, cleavage of ribonucleotides incorporated into amplification products otherwise comprised of deoxyribonucleotides, photochemical cleavage or cleavage of a peptide linker. After the linearization operation a sequencing primer can be delivered to the flow cell under conditions for hybridization of the sequencing primer to the target nucleic acids that are to be sequenced.

A flow cell can then be contacted with an SBS extension reagent having modified nucleotides with removable 3' blocks and fluorescent labels under conditions to extend a primer hybridized to each target nucleic acid by a single nucleotide addition. Only a single nucleotide is added to each primer because once the modified nucleotide has been incorporated into the growing polynucleotide chain complementary to the region of the template being sequenced there is no free 3'-OH group available to direct further sequence extension and therefore the polymerase cannot add further nucleotides. The SBS extension reagent can be removed and replaced with scan reagent containing components that protect the sample under excitation with radiation. Example components for scan reagent are described in U.S. Patent Application Publication No. 2008/0280773 A1 and U.S. patent application Ser. No. 13/018,255, each of which is incorporated herein by reference. The extended nucleic acids can then be fluorescently detected in the presence of scan reagent. Once the fluorescence has been detected, the 3' block may be removed using a deblock reagent that is appropriate to the blocking group used. Example deblock reagents that are useful for respective blocking groups are described in WO004018497, US 2007/0166705A1 and U.S. Pat. No. 7,057,026, each of which is incorporated herein by reference. The deblock reagent can be washed away leaving target nucleic acids hybridized to extended primers having 3'-OH groups that are now competent for addition of a further nucleotide. Accordingly the cycles of adding extension reagent, scan reagent, and deblock reagent, with optional washes between one or more of the operations, can be repeated until a desired sequence is obtained. The above cycles can be carried out using a single extension reagent delivery operation per cycle when each of the modified nucleotides has a different label attached thereto, known to correspond to the particular base. The different labels facilitate discrimination between the nucleotides added during each incorporation operation. Alternatively, each cycle can include separate operations of extension reagent delivery followed by separate operations of scan reagent delivery and detection, in which case two or more of the nucleotides can have the same label and can be distinguished based on the known order of delivery.

Although the sequencing operation has been discussed above with respect to a particular SBS protocol, it will be understood that other protocols for sequencing any of a variety of other molecular analyses can be carried out as desired.

Then, the one or more processors of the system receive the sequencing data for subsequent analysis. The sequencing data may be formatted in various manners, such as in a .BAM file. The sequencing data may include, for example, a number of sample reads. The sequencing data may include a plurality of sample reads that have corresponding sample sequences of the nucleotides. Although only one sample read is discussed, it should be understood that the sequencing data may include, for example, hundreds, thousands, hundreds of thousands, or millions of sample reads. Different sample reads may have different numbers of nucleotides. For example, a sample read may range between 10 nucleotides to about 500 nucleotides or more. The sample reads may span the entire genome of the source(s). As one example, the sample reads are directed toward predetermined genetic loci, such as those genetic loci having suspected STRs or suspected SNPs.

Each sample read may include a sequence of nucleotides, which may be referred to as a sample sequence, sample fragment or a target sequence. The sample sequence may include, for example, primer sequences, flanking sequences, and a target sequence. The number of nucleotides within the sample sequence may include 30, 40, 50, 60, 70, 80, 90, 100 or more. In some implementations, one or more the sample reads (or sample sequences) includes at least 150 nucleotides, 200 nucleotides, 300 nucleotides, 400 nucleotides, 500 nucleotides, or more. In some implementations, the sample reads may include more than 1000 nucleotides, 2000 nucleotides, or more. The sample reads (or the sample sequences) may include primer sequences at one or both ends.

Next, the one or more processors analyze the sequencing data to obtain potential variant call(s) and a sample variant frequency of the sample variant call(s). The operation may also be referred to as a variant call application or variant caller. Thus, the variant caller identifies or detects variants and the variant classifier classifies the detected variants as somatic or germline. Alternative variant callers may be utilized in accordance with implementations herein, wherein different variant callers may be used based on the type of sequencing operation being performed, based on features of the sample that are of interest and the like. One non-limiting example of a variant call application, such as the Pisces™ application by Illumina Inc. (San Diego, CA) hosted at https://github.com/Illumina/Pisces and described in the article Dunn, Tamsen & Berry, Gwenn & Emig-Agius, Dorothea & Jiang, Yu & Iyer, Anita & Udar, Nitin & Stromberg, Michael. (2017). Pisces: An Accurate and Versatile Single Sample Somatic and Germline Variant Caller. 595-595. 10.1145/3107411.3108203, the complete subject matter of which is expressly incorporated herein by reference in its entirety.

Such a variant call application can comprise four sequentially executed modules:

(1) Pisces Read Stitcher: Reduces noise by stitching paired reads in a BAM (read one and read two of the same molecule) into consensus reads. The output is a stitched BAM.

(2) Pisces Variant Caller: Calls small SNVs, insertions and deletions. Pisces includes a variant-collapsing algorithm to coalesce variants broken up by read boundaries, basic filtering algorithms, and a simple Poisson-based variant confidence-scoring algorithm. The output is a VCF.

(3) Pisces Variant Quality Recalibrator (VQR): In the event that the variant calls overwhelmingly follow a pattern associated with thermal damage or FFPE deamination, the VQR step will downgrade the variant Q score of the suspect variant calls. The output is an adjusted VCF.

(4) Pisces Variant Phaser (Scylla): Uses a read-backed greedy clustering method to assemble small variants into complex alleles from clonal subpopulations. This allows for the more accurate determination of functional consequence by downstream tools. The output is an adjusted VCF.

Additionally or alternatively, the operation may utilize the variant call application Strelka™ application by Illumina Inc. hosted at https://github.com/Illumina/strelka and described in the article T Saunders, Christopher & Wong, Wendy & Swamy, Sajani & Becq, Jennifer & J Murray, Lisa & Cheetham, Keira. (2012). Strelka: Accurate somatic small-variant calling from sequenced tumor-normal sample pairs. Bioinformatics (Oxford, England). 28. 1811-7. 10.1093/bioinformatics/bts271, the complete subject matter of which is expressly incorporated herein by reference in its entirety. Furthermore, additionally or alternatively, the operation may utilize the variant call application Strelka2™ application by Illumina Inc. hosted at https://github.com/Illumina/strelka and described in the article Kim, S., Scheffler, K., Halpern, A. L., Bekritsky, M. A., Noh, E., Milberg, M., Chen, X., Beyter, D., Krusche, P., and Saunders, C. T. (2017). Strelka2: Fast and accurate variant calling for clinical sequencing applications, the complete subject matter of which is expressly incorporated herein by reference in its entirety. Moreover, additionally or alternatively, the operation may utilize a variant annotation/call tool, such as the Nirvana™ application by Illumina Inc. hosted at https://github.com/Illumina/Nirvana/wiki and described in the article Stromberg, Michael & Roy, Rajat & Lajugie, Julien & Jiang, Yu & Li, Haochen & Margulies, Elliott. (2017). Nirvana: Clinical Grade Variant Annotator. 596-596. 10.1145/3107411.3108204, the complete subject matter of which is expressly incorporated herein by reference in its entirety.

Such a variant annotation/call tool can apply different algorithmic techniques such as those disclosed in Nirvana:

a. Identifying all overlapping transcripts with Interval Array: For functional annotation, we can identify all transcripts overlapping a variant and an interval tree can be used. However, since a set of intervals can be static, we were able to further optimize it to an Interval Array. An interval tree returns all overlapping transcripts in O(min(n,k lg n)) time, where n is the number of intervals in the tree and k is the number of overlapping intervals. In practice, since k is really small compared to n for most variants, the effective runtime on interval tree would be O(k lg n). We improved to O(lg n+k) by creating an interval array where all intervals are stored in a sorted array so that we only need to find the first overlapping interval and then enumerate through the remaining (k−1).

b. CNVs/SVs (Yu): annotations for Copy Number Variation and Structural Variants can be provided. Similar to the annotation of small variants, transcripts overlapping with the SV and also previously reported structural variants can be annotated in online databases. Unlike the small variants, not all overlapping transcripts need be annotated, since too many transcripts will be overlapped with a large SVs. Instead, all overlapping transcripts can be annotated that belong to a partial overlapping gene. Specifically, for these transcripts, the impacted introns, exons and the consequences caused by the structural variants can be reported. An option to allow output all overlapping transcripts is available, but the basic information for these transcripts can be reported, such as gene symbol, flag whether it is canonical overlap or partial overlapped with the transcripts. For each SV/CNV, it is also of interest to know if these variants have been studied and their frequencies in different populations. Hence, we reported overlapping SVs in external databases, such as 1000 genomes, DGV and ClinGen. To avoid using an arbitrary cutoff to determine which SV is overlapped, instead all overlapping transcripts can be used and the reciprocal overlap can be calculated, i.e. the overlapping length divided by the minimum of the length of these two SVs.

c. Reporting supplementary annotations: Supplementary annotations are of two types: small and structural variants (SVs). SVs can be modeled as intervals and use the interval array discussed above to identify overlapping SVs. Small variants are modeled as points and matched by position and (optionally) allele. As such, they are searched using a binary-search-like algorithm. Since the supplementary annotation database can be quite large, a much smaller index is created to map chromosome positions to file locations where the supplementary annotation resides. The index is a sorted array of objects (made up of chromosome position and file location) that can be binary searched using position. To keep the index size small, multiple positions (up to a certain max count) are compressed to one object that stores the values for the first position and only deltas for subsequent positions. Since we use Binary search, the runtime is O(lg n), where n is the number of items in the database.

d. VEP cache files e. Transcript Database: The Transcript Cache (cache) and Supplementary database (SAdb) files are serialized dump of data objects such as transcripts and supplementary annotations. We use Ensembl VEP cache as our data source for cache. To create the cache, all transcripts are inserted in an interval array and the final state of the array is stored in the cache files. Thus, during annotation, we only need to load a pre-computed interval array and perform searches on it. Since the cache is loaded up in memory and searching is very fast (described above), finding overlapping transcripts is extremely quick in Nirvana (profiled to less than 1% of total runtime?).

f. Supplementary Database: The data sources for SAdb are listed under supplementary material. The SAdb for small variants is produced by a k-way merge of all data sources such that each object in the database (identified by reference name and position) holds all relevant supplementary annotations. Issues encountered during parsing data source files have been documented in detail in Nirvana's home page. To limit memory usage, only the SA index is loaded up in memory. This index allows a quick lookup of the file location for a supplementary annotation. However, since the data has to be fetched from disk, adding supplementary annotation has been identified as Nirvana's largest bottleneck (profiled at ~30% of total runtime.)

g. Consequence and Sequence Ontology: Nirvana's functional annotation (when provided) follows the Sequence Ontology (SO) (http://www.sequenceontology.org/) guidelines. On occasions, we had the opportunity to identify issues in the current SO and collaborate with the SO team to improve the state of annotation.

Such a variant annotation tool can include pre-processing. For example, Nirvana included a large number of annotations from External data sources, like ExAC, EVS, 1000 Genomes project, dbSNP, ClinVar, Cosmic, DGV and ClinGen. To make full use of these databases, we have to sanitize the information from them. We implemented different strategy to deal with different conflicts that exist from different data sources. For example, in case of multiple dbSNP entries for the same position and alternate allele, we join all ids into a comma separated list of ids; if there are multiple entries with different CAF values for the same allele, we use the first CAF value. For conflicting ExAC and EVS entries, we consider the number of sample counts and the entry with higher sample count is used. In 1000 Genome Projects, we removed the allele frequency of the conflicting allele. Another issue is inaccurate information. We mainly extracted the allele frequencies information from 1000 Genome Projects, however, we noticed that for GRCh38, the allele frequency reported in the info field did not exclude samples with genotype not available, leading to deflated frequencies for variants which are not available for all samples. To guarantee the accuracy of our annotation, we use all of the individual level genotype to compute the true allele frequencies. As we know, the same variants can have different representations based on different alignments. To make sure we can accurately report the information for already identified variants, we have to preprocess the variants from different resources to make them have consistent representation. For all external data sources, we trimmed alleles to remove duplicated nucleotides in both reference allele and alternative allele. For ClinVar, we directly parsed the xml file we performed a five-prime alignment for all variants, which is often used in vcf file. Different databases can contain the same set of information. To avoid unnecessary duplicates, we removed some duplicated information. For example, we removed variants in DGV which has data source as 1000 genome projects, since we already reported these variants in 1000 genomes with more detailed information.

In accordance with at least some implementations, the variant call application provides calls for low frequency variants, germline calling and the like. As non-limiting example, the variant call application may run on tumor-only samples and/or tumor-normal paired samples. The variant call application may search for single nucleotide variations (SNV), multiple nucleotide variations (MNV), indels and the like. The variant call application identifies variants, while filtering for mismatches due to sequencing or sample preparation errors. For each variant, the variant caller identifies the reference sequence, a position of the variant, and the potential variant sequence(s) (e.g., A to C SNV, or AG to A deletion). The variant call application identifies the sample sequence (or sample fragment), a reference sequence/fragment, and a variant call as an indication that a variant is present. The variant call application may identify raw fragments, and output a designation of the raw fragments, a count of the number of raw fragments that verify the potential variant call, the position within the raw fragment at which a supporting variant occurred and other relevant information. Non-limiting examples of raw fragments include a duplex stitched fragment, a simplex stitched fragment, a duplex un-stitched fragment and a simplex un-stitched fragment.

The variant call application may output the calls in various formats, such as in a .VCF or .GVCF file. By way of example only, the variant call application may be included in a MiSeqReporter pipeline (e.g., when implemented on the MiSeq® sequencer instrument). Optionally, the application may be implemented with various workflows. The analysis may include a single protocol or a combination of protocols that analyze the sample reads in a designated manner to obtain desired information.

Then, the one or more processors perform a validation operation in connection with the potential variant call. The validation operation may be based on a quality score, and/or a hierarchy of tiered tests, as explained hereafter. When the validation operation authenticates or verifies that the potential variant call, the validation operation passes the variant call information (from the variant call application) to the sample report generator. Alternatively, when the validation operation invalidates or disqualifies the potential variant call, the validation operation passes a corresponding indication (e.g., a negative indicator, a no call indicator, an in-valid call indicator) to the sample report generator. The validation operation also may pass a confidence score related to a degree of confidence that the variant call is correct or the in-valid call designation is correct.

Next, the one or more processors generate and store a sample report. The sample report may include, for example, information regarding a plurality of genetic loci with respect to the sample. For example, for each genetic locus of a predetermined set of genetic loci, the sample report may at least one of provide a genotype call; indicate that a genotype call cannot be made; provide a confidence score on a certainty of the genotype call; or indicate potential problems with an assay regarding one or more genetic loci. The sample report may also indicate a gender of an individual that provided a sample and/or indicate that the sample include multiple sources. As used herein, a "sample report" may include digital data (e.g., a data file) of a genetic locus or predetermined set of genetic locus and/or a printed report of the genetic locus or the set of genetic loci. Thus, generating or providing may include creating a data file and/or printing the sample report, or displaying the sample report.

The sample report may indicate that a variant call was determined, but was not validated. When a variant call is determined invalid, the sample report may indicate additional information regarding the basis for the determination to not validate the variant call. For example, the additional information in the report may include a description of the raw fragments and an extent (e.g., a count) to which the raw fragments support or contradicted the variant call. Additionally or alternatively, the additional information in the report may include the quality score obtained in accordance with implementations described herein.

Variant Call Application

Implementations disclosed herein include analyzing sequencing data to identify potential variant calls. Variant calling may be performed upon stored data for a previously performed sequencing operation. Additionally or alternatively, it may be performed in real time while a sequencing operation is being performed. Each of the sample reads is assigned to corresponding genetic loci. The sample reads may be assigned to corresponding genetic loci based on the sequence of the nucleotides of the sample read or, in other words, the order of nucleotides within the sample read (e.g., A, C, G, T). Based on this analysis, the sample read may be designated as including a possible variant/allele of a particular genetic locus. The sample read may be collected (or aggregated or binned) with other sample reads that have been designated as including possible variants/alleles of the genetic locus. The assigning operation may also be referred to as a calling operation in which the sample read is identified as being possibly associated with a particular genetic position/locus. The sample reads may be analyzed to locate one or more identifying sequences (e.g., primer sequences) of nucleotides that differentiate the sample read from other sample reads. More specifically, the identifying sequence(s) may identify the sample read from other sample reads as being associated with a particular genetic locus.

The assigning operation may include analyzing the series of n nucleotides of the identifying sequence to determine if the series of n nucleotides of the identifying sequence effectively matches with one or more of the select sequences. In particular implementations, the assigning operation may include analyzing the first n nucleotides of the sample sequence to determine if the first n nucleotides of the sample sequence effectively matches with one or more of the select sequences. The number n may have a variety of values, which may be programmed into the protocol or entered by a user. For example, the number n may be defined as the number of nucleotides of the shortest select sequence within the database. The number n may be a predetermined number. The predetermined number may be, for example, 10, 11, 12, 13, 14, 15, 16, 17, 18, 19, 20, 21, 22, 23, 24, 25, 26, 27, 28, 29, or 30 nucleotides. However, fewer or more nucleotides may be used in other implementations. The number n may also be selected by an individual, such as a user of the system. The number n may be based on one or more conditions. For instance, the number n may be defined as the number of nucleotides of the shortest primer sequence within the database or a designated number, whichever is the smaller number. In some implementations, a minimum value for n may be used, such as 15, such that any primer sequence that is less than 15 nucleotides may be designated as an exception.

In some cases, the series of n nucleotides of an identifying sequence may not precisely match the nucleotides of the select sequence. Nonetheless, the identifying sequence may effectively match the select sequence if the identifying sequence is nearly identical to the select sequence. For example, the sample read may be called for a genetic locus if the series of n nucleotides (e.g., the first n nucleotides) of the identifying sequence match a select sequence with no more than a designated number of mismatches (e.g., 3) and/or a designated number of shifts (e.g., 2). Rules may be established such that each mismatch or shift may count as a difference between the sample read and the primer sequence. If the number of differences is less than a designated number, then the sample read may be called for the corresponding genetic locus (i.e., assigned to the corresponding genetic locus). In some implementations, a matching score may be determined that is based on the number of differences between the identifying sequence of the sample read and the select sequence associated with a genetic locus. If the matching score passes a designated matching threshold, then the genetic locus that corresponds to the select sequence may be designated as a potential locus for the sample read. In some implementations, subsequent analysis may be performed to determine whether the sample read is called for the genetic locus.

If the sample read effectively matches one of the select sequences in the database (i.e., exactly matches or nearly matches as described above), then the sample read is assigned or designated to the genetic locus that correlates to the select sequence. This may be referred to as locus calling or provisional-locus calling, wherein the sample read is called for the genetic locus that correlates to the select sequence. However, as discussed above, a sample read may be called for more than one genetic locus. In such implementations, further analysis may be performed to call or assign the sample read for only one of the potential genetic loci. In some implementations, the sample read that is compared to the database of reference sequences is the first read from paired-end sequencing. When performing paired-end sequencing, a second read (representing a raw fragment) is obtained that correlates to the sample read. After assigning, the subsequent analysis that is performed with the assigned reads may be based on the type of genetic locus that has been called for the assigned read.

Next, the sample reads are analyzed to identify potential variant calls. Among other things, the results of the analysis identify the potential variant call, a sample variant frequency, a reference sequence and a position within the genomic sequence of interest at which the variant occurred. For example, if a genetic locus is known for including SNPs, then the assigned reads that have been called for the genetic locus may undergo analysis to identify the SNPs of the assigned reads. If the genetic locus is known for including polymorphic repetitive DNA elements, then the assigned reads may be analyzed to identify or characterize the polymorphic repetitive DNA elements within the sample reads. In some implementations, if an assigned read effectively matches with an STR locus and an SNP locus, a warning or flag may be assigned to the sample read. The sample read may be designated as both an STR locus and an SNP locus. The analyzing may include aligning the assigned reads in accordance with an alignment protocol to determine sequences and/or lengths of the assigned reads. The alignment protocol may include the method described in International Patent Application No. PCT/US2013/030867 (Publication No. WO 2014/142831), filed on Mar. 15, 2013, which is herein incorporated by reference in its entirety.

Then, the one or more processors analyze raw fragments to determine whether supporting variants exist at corresponding positions within the raw fragments. Various types of raw fragments may be identified. For example, the variant caller may identify a type of raw fragment that exhibits a variant that validates the original variant call. For example, the type of raw fragment may represent a duplex stitched fragment, a simplex stitched fragment, a duplex un-stitched fragment or a simplex un-stitched fragment. Optionally other raw fragments may be identified instead of or in addition to the foregoing examples. In connection with identifying each type of raw fragment, the variant caller also identifies the position, within the raw fragment, at which the supporting variant occurred, as well as a count of the number of raw fragments that exhibited the supporting variant. For example, the variant caller may output an indication that 10 reads of raw fragments were identified to represent duplex stitched fragments having a supporting variant at a particular position X. The variant caller may also output indication that five reads of raw fragments were identified to represent simplex un-stitched fragments having a supporting variant at a particular position Y. The variant caller may also output a number of raw fragments that corresponded to reference sequences and thus did not include a supporting variant that would otherwise provide evidence validating the potential variant call at the genomic sequence of interest.

Next, a count is maintained of the raw fragments that include supporting variants, as well as the position at which the supporting variant occurred. Additionally or alternatively, a count may be maintained of the raw fragments that did not include supporting variants at the position of interest (relative to the position of the potential variant call in the sample read or sample fragment). Additionally or alternatively, a count may be maintained of raw fragments that correspond to a reference sequence and do not authenticate or confirm the potential variant call. The information determined is output to the variant call validation application, including a count and type of the raw fragments that support the potential variant call, positions of the supporting variance in the raw fragments, a count of the raw fragments that do not support the potential variant call and the like.

When a potential variant call is identified, the process outputs an indicating of the potential variant call, the variant sequence, the variant position and a reference sequence associated therewith. The variant call is designated to represent a "potential" variant as errors may cause the call process to identify a false variant. In accordance with implementations herein, the potential variant call is analyzed to reduce and eliminate false variants or false positives. Additionally or alternatively, the process analyzes one or more raw fragments associated with a sample read and outputs a corresponding variant call associated with the raw fragments.

Variant Classifier

FIG. 1A shows one implementation of variant calling by a trained variant classifier disclosed herein. The trained variant classifier includes a convolutional neural network (CNN). The input to the variant classifier is an array of input features (described with reference to FIG. 2). The array is encoded from reads (or sequence reads). Bases (or nucleotides) in reads are identified or base called through primary analysis of sequencing data produced by genome analyzers using sequencing protocols like sequencing-by-synthesis (SBS). Candidate variants at candidate variant sites spanning in the reads are identified by an alignment process, one implementation of which is discussed below.

Recent hardware and software improvements have resulted in a significant increase in the data output capacity of genome analyzers such as Illumina sequencing systems (e.g., HiSegX™, HiSeg3000™, HiSeg4000™, NovaSeq 6000™, MiSegDx™, Firefly™). Greater than 33 gigabyte (GB) of sequence output, comprising approximately 300 million 2×100 base pair (bp) reads, can now be routinely generated within 10 days. In one implementation, the technology disclosed uses Illumina's Consensus Assessment of Sequence And Variation (CASAVA) software, which seamlessly processes this large volume of sequencing data, supporting sequencing of large or small genomes, targeted deoxyribonucleic acid (DNA) resequencing, and ribonucleic acid (RNA) sequencing.

CASAVA can analyze sequencing data (e.g., image data, detection data) generated by the genome analyzers in two steps. In the first step (primary analysis), a Sequencing Control Software Real Time Analysis (SCS/RTA), which runs on an instrument computer, performs real-time data analysis and base calling. Base calling produces reads. In the second step, CASAVA performs complete secondary analysis of the reads by aligning the reads against a reference read (or reference genome) to determine sequence differences (e.g., candidate variants like single-base polymorphisms (SNPs), insertions/deletions (indels)), a larger overall sequence, or the like. Algorithms for the alignment of reads and detection of candidate variants are described in Illumina's patent application No. WO05068089 and Illumina's technical note titled "Complete Secondary Analysis Workflow for the Genome Analyzer" (available at https://www.illumina.com/documents/products/technotes/technote_casava_secondary_analysis.pdf), which are incorporated by reference as if fully set forth herein.

Figure 2:
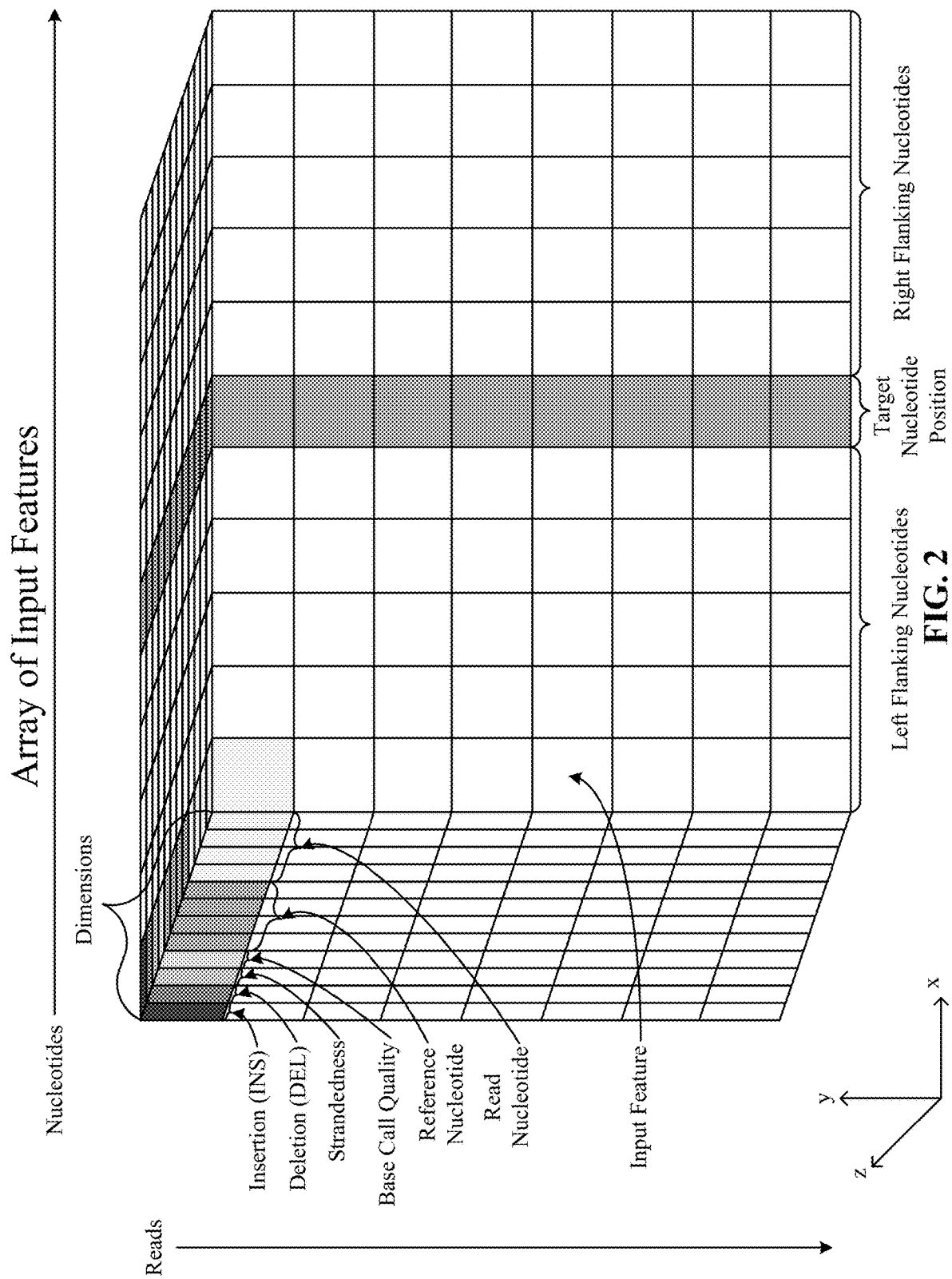
FIG. 2 is one implementation of an array of input features that is fed to the convolutional neural network of the variant classifier of FIG. 1A.

In other implementations, the primary and secondary analysis are performed by other Illumina Applications such as Whole Genome Sequencing and DRAGEN, additional details of which can be found at https://www.illumina.com/products/by-type/informatics-products/basespace-sequence-hub/apps/whole-genome-sequencing.html?langseHus/and https://support.illumina.com/content/dam/illumina-marketing/documents/products/technotes/illumina-proactive-technical-note-1000000052503.pdf, which are incorporated by reference as if fully set forth herein Array of Input Features FIG. 2 is one implementation of the array of input features that is fed to the convolutional neural network of the variant classifier of FIG. 1A. The array encodes a group of reads that are aligned to a reference read. Each read in the group includes a target base position (highlighted in grey). The target base position corresponds to a candidate variant at a candidate variant site (e.g., SNP, indel). The target base position is flanked by or padded to bases on each side (e.g., left flanking bases, right flanking bases). In some implementations, the number of left flanking bases is the same as the number of right flanking bases. In other implementations, the number of left flanking bases is different than the number of right flanking bases. The number of flanking bases on each side can be 30, 70, 90, 110, and so on.

The group of reads is row-wise arranged in the array along the x-axis (i.e., along a first spatial dimension, e.g., height dimension), in accordance with one implementation. That is, each row in the array represents a read that is aligned to the reference read and includes the target base position. Base positions in the reads are column-wise arranged in the array along the y-axis (i.e., along a second spatial dimension, e.g., width dimension), in accordance with one implementation. That is, each column in the array represents bases in the reads at a particular ordinal position.

Each unit in the array is an input feature (depicted by a front-facing box in FIG. 2). Each input feature in the array corresponds to a base in the reads. Each input feature in the array has a plurality of dimensions. The plurality of dimensions is arranged in the array along the z-axis (e.g., along a depth, channel, feature, or fibre dimension), in accordance with one implementation.

In one implementation, the plurality of dimensions includes (i) a first dimension set identifying the base, (ii) a second dimension set identifying a reference base aligned to the base, (iii) a third dimension set identifying a base call accuracy score of the base, (iv) a fourth dimension set identifying strandedness (i.e., DNA strandedness) of the base, (v) a fifth dimension set identifying an insertion count (INS) of changes adjoining a position of the base, (vi) a sixth dimension set identifying a deletion flag (DEL) at the position of the base.

In other implementations, the array can be considered a volume. In yet other implementations, the array can be considered a tensor. In some implementations, the array represents a read pileup around a candidate variant. In some implementations, the dimensions of an input feature can be considered input channels.

In one example, each input feature has twelve dimensions. Then, the first dimension set includes four dimensions that use one-hot encoding to identify the base of the input features. The base can be Adenine (A), Cytosine (C), Guanine (G), or Thymine (T). The second dimension set also includes four dimensions that use one-hot encoding to identify the reference base aligned to the base. The reference base can also be A, C, G, or T.

In one-hot encoding, each base in a sequence is encoded with a binary vector of four bits, with one of the bits being hot (i.e., 1) while other being 0. For instance, A=(1, 0, 0, 0), C=(0, 1, 0, 0), G=(0, 0, 1, 0), and T=(0, 0, 0, 1). In some implementations, an unknown base is encoded as N=(0, 0, 0, 0).

Accordingly, each input feature "locally" encodes alignment between the base in a read and the corresponding reference base in the reference read. As a result, when kernels of convolution filters of the convolutional neural network of the variant classifier of FIG. 1A are applied over a window of input features in the array, they take into account so-called "one-on-one contextual dependencies" between bases in the reference read and bases in the reads, as well as so-called "adjacent contextual dependencies" between bases in the reads.

The third, fourth, fifth, and sixth dimension sets each include one dimension to respectively identify the base call accuracy score of the base as a continuous number, the strandedness of the base using one-hot encoding (e.g., 0 for forward strand and 1 for reverse strand), the insertion count (INS) of changes adjoining a position of the base as numbers (e.g., 4 for 4 inserted bases), and the deletion flag (DEL) at the position of the base as numbers (e.g., 1111 for 4 deleted base positions). In FIG. 2, the six dimension sets of an input feature are graphically distinguished using different shades of grey.

In some implementations, the mapping quality of each read is also encoded in the array. The mapping quality (MAPA) is a number (e.g., 40) that can be encoded in an additional dimension or channel of each unit or each input feature in the array.

Regarding the base call accuracy score, in one implementation, it can be identified as a Phred quality score (e.g., Q10, Q20, Q30, Q40, Q50) defined as property that is logarithmically related to the base calling error probabilities $(P)^2$. Additional information about the base call accuracy score can be found in Illumina's technical notes titled "Quality Scores for Next-Generation Sequencing" and "Understanding Illumina Quality Scores" (available at https://www.illumina.com/documents/products/technotes/technote Q-Scores.pdf, https://www.illumina.com/documents/products/technotes/technote understanding quality scores .pdf), which are incorporated by reference as if fully set forth herein.

Regarding the insertion count (INS) of changes adjoining a position of the base, in one implementation, it can identify a number of bases inserted before or after the base. Regarding the deletion flag (DEL) at the position of the base, in one implementation, it can identify an undetermined, unread, unidentified, empty, or deleted base at the position of the base.

In one implementation, the dimensionality of the array is 100×221×12, where: (a) 100 represents the number of reads in the group that are aligned to the reference read and span the candidate variant sites at the target base position; (b) 221 represents the number of base positions in each of the reads, with the target base position at the $111^{th}$ ordinal position flanked by 110 base positions on each side; and (c) 12 represents the local dimensionality of each input feature in the array, i.e., the number of dimensions of each of the input features.

In other implementations, the input features can have different numbers of dimensions, which can be further segmented into dimension sets of varying sizes using a different encoding scheme.

In yet other implementations, one-hot encoding may be replaced by other encoding schemes such as a dense or real-valued encoding scheme based on an embedding space or embedding matrix produced by a trained neural network. In yet further implementations, the encoding schemes can be based on quantitative or numerical data type, qualitative data type, discreet data type, continuous data type (with lower and upper bounds), integer data type (with lower and upper bounds), nominal data type, ordinal or ranked data type, categorical data type, interval data type, and/or ratio data type. For example, the encoding can be based on, or any combination thereof, real values between 0 and 1, continuous values such as red, green, blue (RGB) values between 0 and 256, hexadecimal values, size of a particular dimension (e.g., height and width), a set of different values and data types, and others.

Variant Classifier CNN Architecture

Figure 3A:
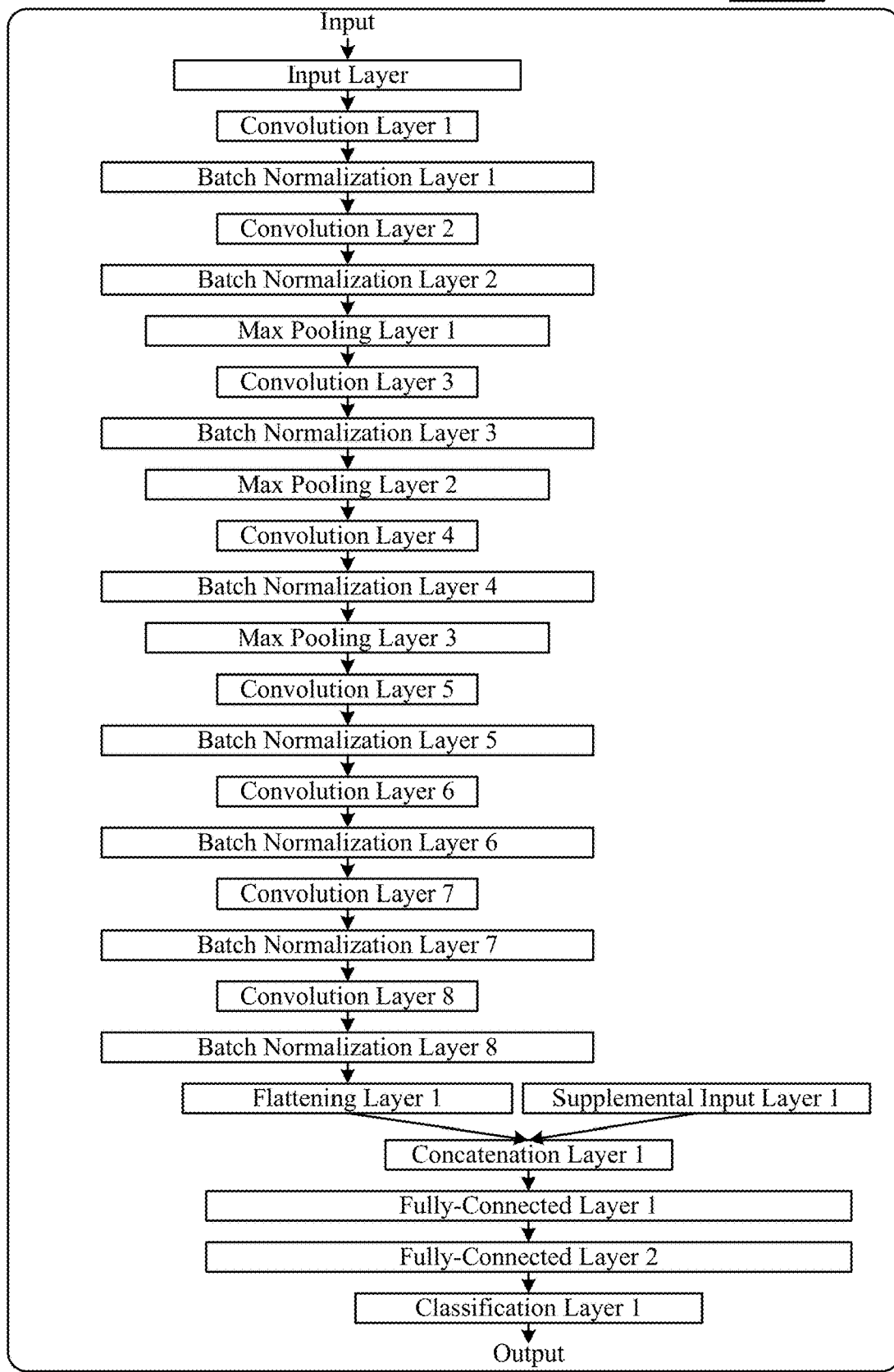
FIG. 3A illustrates one implementation of architecture of the convolutional neural network of the variant classifier of FIG. 1A.

As discussed above, the array of input features that is fed to the convolutional neural network of the variant classifier of FIG. 1A. FIG. 3A illustrates one implementation of architecture 300A of the convolutional neural network of the variant classifier of FIG. 1A. Specifically, the convolutional neural network architecture illustrated in FIG. 3A has eight convolution layers. The variant classifier convolutional neural network can include an input layer that is followed by a plurality of convolution layers. Some of the convolution layers can be followed by a max pooling (or sampling) layer, with an intermediate batch normalization layer between the convolution layer and the max pooling layer. In the illustrated implementation, the convolutional neural network has eight convolution layers, three max pooling layers, and eight batch normalization layers.

Regarding batch normalization, batch normalization is a method for accelerating deep network training by making data standardization an integral part of the network architecture. Batch normalization can adaptively normalize data even as the mean and variance change over time during training. It works by internally maintaining an exponential moving average of the batch-wise mean and variance of the data seen during training. The main effect of batch normalization is that it helps with gradient propagation—much like residual connections—and thus allows for deep networks. Some very deep networks can only be trained if they include multiple Batch Normalization layers.

Batch normalization can be seen as yet another layer that can be inserted into the model architecture, just like the fully connected or convolutional layer. The BatchNormalization layer is typically used after a convolutional or densely connected layer. It can also be used before a convolutional or densely connected layer. Both implementations can be used by the technology disclosed. The BatchNormalization layer takes an axis argument, which specifies the feature axis that should be normalized. This argument defaults to −1, the last axis in the input tensor. This is the appropriate value when using Dense layers, Conv1D layers, RNN layers, and Conv2D layers with data_format set to "channels_last". But in the niche use case of Conv2D layers with data_format set to "channels_first", the features axis is axis 1; the axis argument in BatchNormalization can be set to 1.

Batch normalization provides a definition for feed-forwarding the input and computing the gradients with respect to the parameters and its own input via a backward pass. In practice, batch normalization layers are inserted after a convolutional or fully connected layer, but before the outputs are fed into an activation function. For convolutional layers, the different elements of the same feature map—i.e. the activations—at different locations are normalized in the same way in order to obey the convolutional property. Thus, all activations in a mini-batch are normalized over all locations, rather than per activation.

The internal covariate shift is the major reason why deep architectures have been notoriously slow to train. This stems from the fact that deep networks do not only have to learn a new representation at each layer, but also have to account for the change in their distribution.

The covariate shift in general is a known problem in the deep learning domain and frequently occurs in real-world problems. A common covariate shift problem is the difference in the distribution of the training and test set which can lead to suboptimal generalization performance. This problem is usually handled with a standardization or whitening preprocessing step. However, especially the whitening operation is computationally expensive and thus impractical in an online setting, especially if the covariate shift occurs throughout different layers.

The internal covariate shift is the phenomenon where the distribution of network activations change across layers due to the change in network parameters during training. Ideally, each layer should be transformed into a space where they have the same distribution but the functional relationship stays the same. In order to avoid costly calculations of covariance matrices to decorrelate and whiten the data at every layer and step, we normalize the distribution of each input feature in each layer across each mini-batch to have zero mean and a standard deviation of one.

During the forward pass, the mini-batch mean and variance are calculated. With these mini-batch statistics, the data is normalized by subtracting the mean and dividing by the standard deviation. Finally, the data is scaled and shifted with the learned scale and shift parameters. Since normalization is a differentiable transform, the errors are propagated into these learned parameters and are thus able to restore the representational power of the network by learning the identity transform. Conversely, by learning scale and shift parameters that are identical to the corresponding batch statistics, the batch normalization transform would have no effect on the network, if that was the optimal operation to perform. At test time, the batch mean and variance are replaced by the respective population statistics since the input does not depend on other samples from a mini-batch. Another method is to keep running averages of the batch statistics during training and to use these to compute the network output at test time.

The convolution layers can be parametrized by a number of convolution filters (e.g., thirty-two filters) and a convolution window size. The convolution filters can be further parameterized by two spatial dimensions, namely, height and width (e.g., 5×5 or 5×1) and by a third depth, feature, or fibre dimension (e.g., 12, 10, 32). In implementations, the depth dimensionality of the convolution filters of the first convolution layer of the convolutional neural network matches the number of dimensions of the input features of the array.

The convolutional neural network can also include one or more fully-connected layers. In the illustrated embodiment, the convolutional neural network includes two fully-connected layers. In implementations, the convolutional neural network processes the group of reads through the convolution layers and concatenates output of the convolution layers with corresponding empirical variant score (EVS) features provided by a supplemental input layer. The supplemental input layer of the convolutional neural network can be different from the input layer that provides the array as input to the first convolution layer of the convolutional neural network. In one implementation, the output of the last convolution layer of the convolutional neural network is flattened by a flattening layer of the convolutional neural network and then combined with the EVS features.

Regarding the EVS features, a set of EVS features can be associated with the candidate variant site in the array (e.g., twenty three EVS features for SNPs and twenty two EVS features for indels). Some examples of the EVS features include germline features, RNA-seq features, and Somatic features, Germline SNV features, Germline Indel features, RNA-seq SNV features, RNA-seq Indel features, Somatic SNV features, and Somatic Indel features. Additional examples of the EVS features are provided later in this application under the Section titled "EVS Feature".

Each EVS feature is a number that represents a specific attribute of a candidate variant site. Thus, a set of EVS features of a candidate variant site is identified by a vector of numbers or numerical descriptors, according to one implementation. The EVS feature numbers are fed directly to the convolutional neural network. For instance, GenotypeCategory is 0 for heterozygous sites, 1 for homozygous sites, and 2 for alt-heterozygous sites. Others, like SampleRMSMappingQuality are floating point numbers. RMS stands for Root-Mean Square EVS feature and is determined by summing the squared mapping qualities for each read covering the site, dividing it by the number of reads, and then taking the square root of the results of the division. We observe higher accuracy with the ConservativeGenotypeQuality EVS feature.

After the output of the last convolution layer is concatenated with the EVS features, the convolutional neural network then feeds the result of the concatenation to the fully-connected layers. A classification layer (e.g., softmax layer) following the full-connected layers can produce classification scores for likelihood that each candidate variant at the target base position is a true variant or a false variant. In other implementations, the classification layer can produce classification scores for likelihood that each candidate variant at the target base position is a homozygous variant, a heterozygous variant, a non-variant, or a complex-variant.

FIG. 3B illustrates another implementation of the architecture 300B of the convolutional neural network of the variant classifier of FIG. 1A. FIG. 3B also shows the dimensionality of the input/output at various processing phases of the convolutional neural network. Specifically, the convolutional neural network architecture illustrated in FIG. 3B has seven convolution layers. In this example architecture, the dimensionality of the output produced by a first 5×5 convolution layer with thirty-two filters and a first successive max pooling layer can be 108×48×32; the dimensionality of the output produced by a second 5×5 convolution layer with thirty-two filters and a second successive max pooling layer can be 52×22×32; and the dimensionality of the output produced by a third 5×5 convolution layer with thirty-two filters and a third successive max pooling layer can be 24×9×32. Moving ahead, the dimensionality of the output produced by a fourth 5×5 convolution layer with thirty-two filters and no successive max pooling layer can be 20×5×32; the dimensionality of the output produced by a fifth 5×5 convolution layer with thirty-two filters and no successive max pooling layer can be 16×1×32; the dimensionality of the output produced by a sixth 5×1 convolution layer with thirty-two filters and no successive max pooling layer can be 11×1×32; and the dimensionality of the output produced by a seventh 5×1 convolution layer with thirty-two filters and no successive max pooling layer can be 7×1×32. Moving ahead, the 7×1×32 output can be flattened into a 224 dimensional vector and further concatenated with a 23 or 22 dimensional EVS feature vector to produce a 247 or 246 dimensional concatenated vector. The concatenated vector can be fed to a fully-connected layers with 256 units and then to a classification layer to produce the classification scores.

Figure 3C:
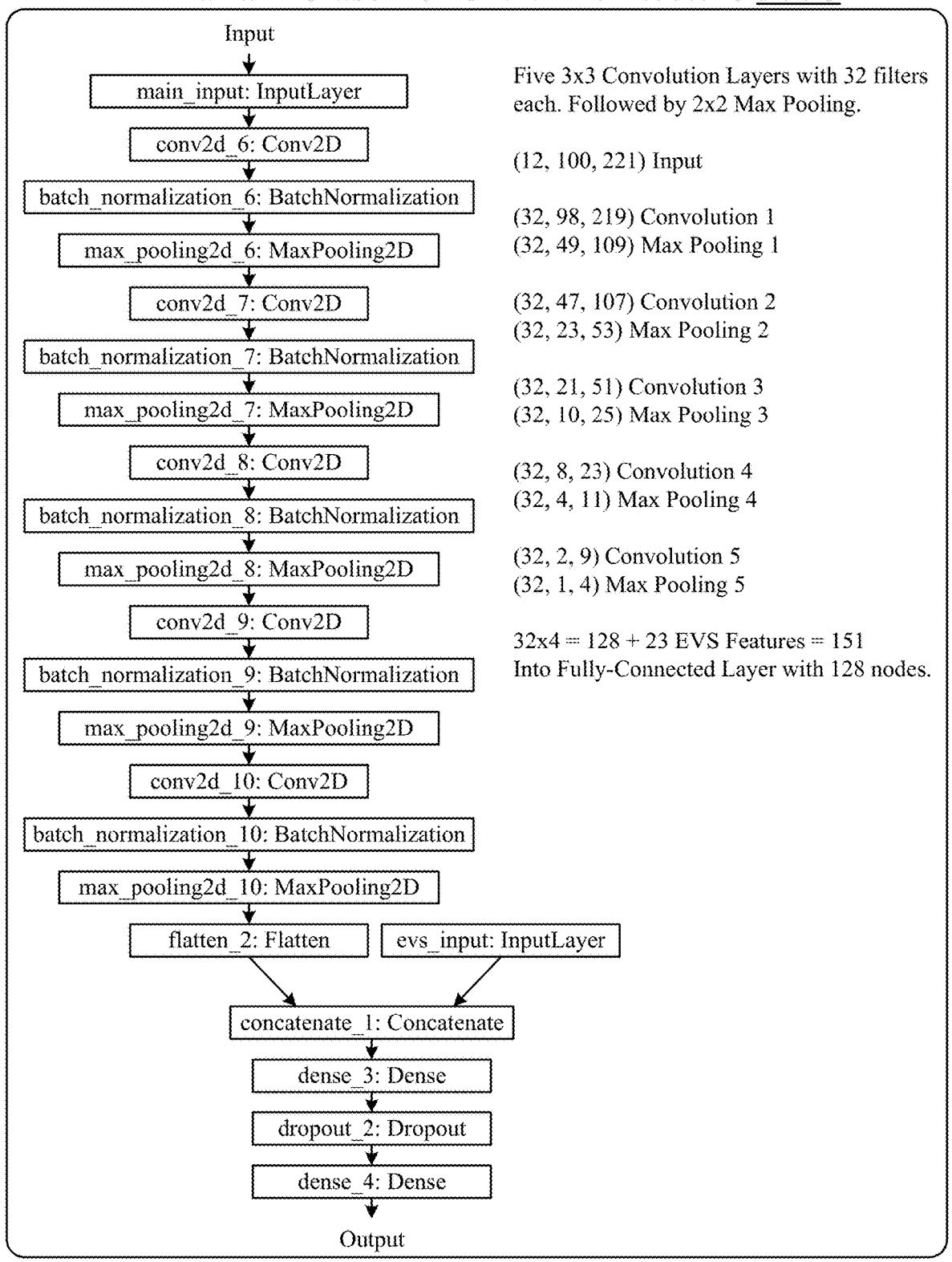
FIG. 3C illustrates yet another implementation of the architecture of the convolutional neural network of the variant classifier of FIG. 1A.

FIG. 3C illustrates yet another implementation of the architecture 300C of the convolutional neural network of the variant classifier of FIG. 1A. Specifically, the convolutional neural network architecture illustrated in FIG. 3C has five convolution layers. In this example architecture, the variant classifier convolutional neural network can include an input layer that is followed by five 3×3 convolution layers with thirty-two convolution filters each. Each convolution layer can be followed by a batch normalization layer and a 2×2 max pooling layer. The convolutional neural network can further include a flattening layer, a supplemental input layer, a concatenation layer, two fully-connected (FC) layers, and a classification layer. FIG. 3C also shows the dimensionality of the input/output at various processing phases of the convolutional neural network.

Figure 3D:
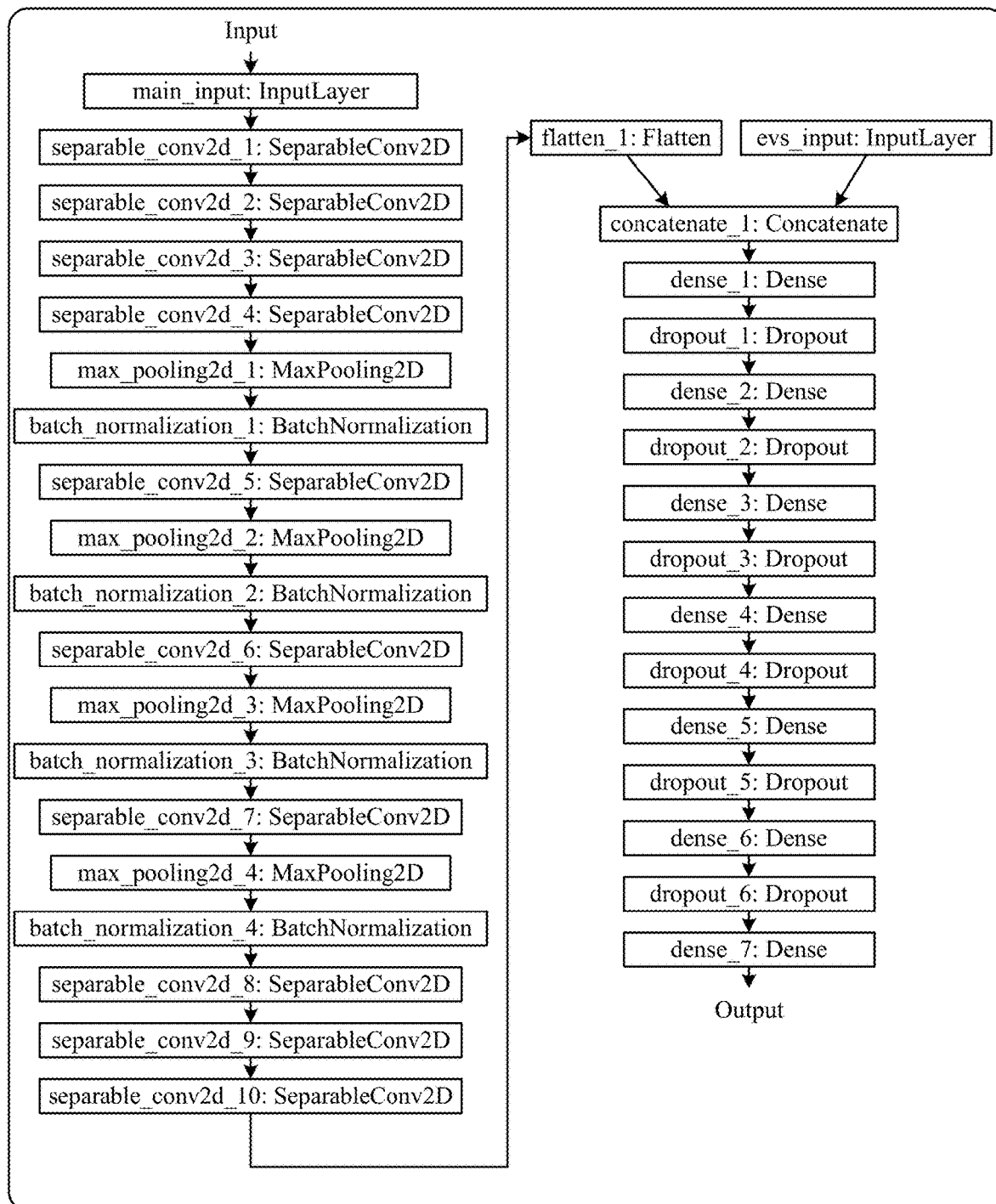
FIG. 3D illustrates yet another implementation of the architecture of the convolutional neural network of the variant classifier of FIG. 1A.

FIG. 3D illustrates yet another implementation of the architecture 300D of the convolutional neural network of the variant classifier of FIG. 1A. Specifically, the convolutional neural network architecture illustrated in FIG. 3D uses depthwise separable convolutions. In contrast to a standard convolution, a depthwise separable convolution performs a separate convolution of each channel of the input data and then performs a pointwise convolution to mix the channels. For additional information about the depthwise separable convolutions, reference can be made to A. G. Howard, M. Zhu, B. Chen, D. Kalenichenko, W. Wang, T. Weyand, M. Andreetto, and H. Adam, "Mobilenets: Efficient Convolutional Neural Networks for Mobile Vision Applications," in arXiv:1704.04861, 2017, which is incorporated by reference as if fully set forth herein.

Variant Classifier FC Network Architecture

FIG. 4A depicts a fully-connected (FC) network 400A in which computation units have full connections to all the computation units of the previous layer. Suppose that a layer has m computation units and the previous layer gives n outputs, then we get a total number of m*n weights.

Figure 4B:
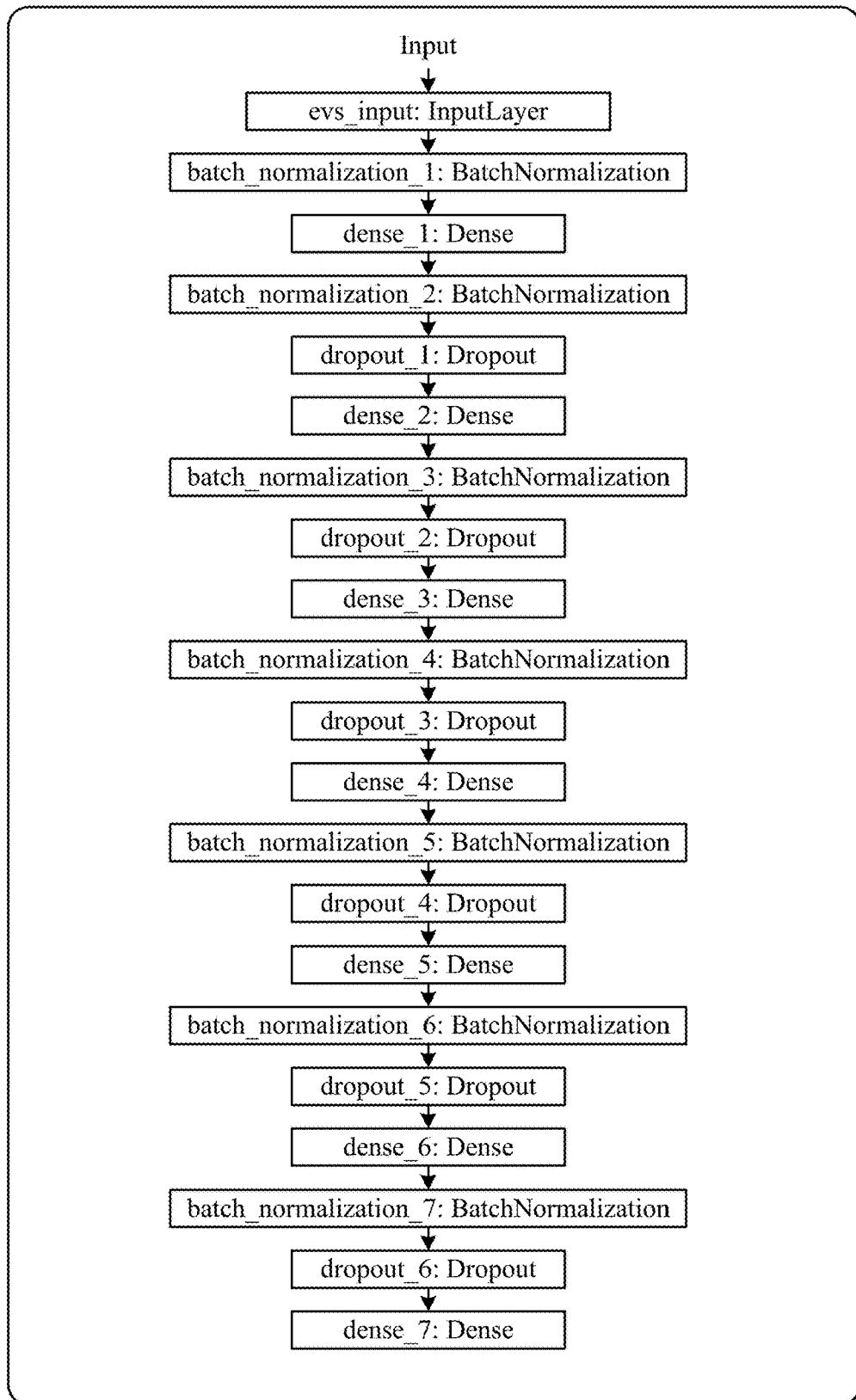
FIG. 4B illustrates one implementation of architecture of the fully-connected neural network of the variant classifier that takes as input only empirical variant score (EVS) features. This architecture does not use any convolutions.

FIG. 4B illustrates one implementation of architecture 400B of the fully-connected neural network of the variant classifier, without any convolution layers. Architecture 400B uses fully-connected layers (also called "dense layers"). In FIG. 4B, there are seven dense layers, interspersed with batch normalization and dropout layers.

In one implementation, the fully-connected neural network of the variant classifier has four fully-connected layers, with 64 units per layer, 10% dropout rate, and a batch normalization layer after each fully-connected layer.

The input to the fully-connected neural network are empirical variant score (EVS) features of a candidate variant site. Each EVS feature is a number that represents a specific attribute of a candidate variant site. Thus, a set of EVS features of a candidate variant site is identified by a vector of numbers or numerical descriptors, according to one implementation. The EVS feature numbers are fed directly to the convolutional neural network. For instance, GenotypeCategory is 0 for heterozygous sites, 1 for homozygous sites, and 2 for alt-heterozygous sites. Others, like SampleRMSMappingQuality are floating point numbers. RMS stands for Root-Mean Square EVS feature and is determined by summing the squared mapping qualities for each read covering the site, dividing it by the number of reads, and then taking the square root of the results of the division. We observe higher accuracy with the ConservativeGenotypeQuality EVS feature.

The input to the fully-connected neural network can be any combination of the EVS feature listed below. That is, an EVS feature vector for a particular candidate variant site being evaluated by the variant caller can be encoded or constructed to include number values for any of the EVS features listed below.

EVS Features

The following lists examples of the EVS features under four categories:

(1) Germline SNV features: GenotypeCategory, SampleRMSMappingQuality, SiteHomopolymerLength, SampleStrandBias, SampleRMSMappingQualityRankSum, SampleReadPosRankSum, RelativeTotalLocusDepth, SampleUsedDepthFraction, ConservativeGenotypeQuality, NormalizedAltHaplotypeCountRatio.

(2) Germline Indel features: GenotypeCategory, SampleIndelRepeatCount, SampleIndelRepeatUnitSize, SampleIndelAlleleBiasLower, SampleIndelAlleleBias, SampleProxyRMSMappingQuality, RelativeTotalLocusDepth, SamplePrimaryAltAlleleDepthFraction, ConservativeGenotypeQuality, InterruptedHomopolymerLength, ContextCompressability, IndelCategory, NormalizedAltHaplotypeCountRatio.

(3) Somatic SNV features: SomaticSNVQualityAndHomRefGermlineGenotype, Normal SampleRelativeTotalLocusDepth, TumorSampleAltAlleleFraction, RMSMappingQuality, ZeroMappingQualityFraction, TumorSampleStrandBias, TumorSampleReadPosRankSum, AlleleCountLogOddsRatio, Normal SampleFilteredDepthFraction, TumorSampleFilteredDepthFraction.

(4) Somatic Indel features: SomaticIndelQualityAndHomRefGermlineGenotype, TumorSampleReadPosRankSum, TumorSampleLogSymmetricStrandOddsRatio, RepeatUnitLength, IndelRepeatCount, RefRepeatCount, InterruptedHomopolymerLength, TumorSampleIndelNoiseLogOdds, TumorNormalIndelAlleleLogOdds, AlleleCountLogOddsRatio.

The following are definitions of the EVS features listed above:

Germline Feature Descriptions:

| | |
|---|---|
| GenotypeCategory | A category variable reflecting the most likely genotype as heterozygous (0), homozygous (1) or alt-heterozygous (2). |
| SampleRMSMappingQuality | RMS mapping quality of all reads spanning the variant in one sample. This feature matches SAMPLE/MQ in the VCF spec. |
| SiteHomopolymerLength | Length of the longest homopolymer containing the current position if this position can be treated as any base. |
| InterruptedHomopolymerLength | One less than the length of the longest interrupted homopolymer in the reference sequence containing the current position. An interrupted homopolymer is a string that has edit distance 1 to a homopolymer. |
| SampleStrandBias | Log ratio of the sample's genotype likelihood computed assuming the alternate allele occurs on only one strand vs both strands (thus positive values indicate bias). |

-continued

| | |
|---|---|
| SampleRMSMappingQualityRankSum | Z-score of Mann-Whitney U test for reference vs alternate allele mapping quality values in one sample. |
| SampleReadPosRankSum | Z-score of Mann-Whitney U test for reference vs alternate allele read positions in one sample. |
| RelativeTotalLocusDepth | Locus depth relative to expectation: this is the ratio of total read depth at the variant locus in all samples over the total expected depth in all samples. Depth at the variant locus includes reads at any mapping quality. Expected depth is taken from the preliminary depth estimation step. This value is set to 1 in exome and targeted analyses, because it is problematic to define expected depth in this case. |
| SampleUsedDepthFraction | The ratio of reads used to genotype the locus over the total number of reads at the variant locus in one sample. Reads are not used if the mapping quality is less than the minimum threshold, if the local read alignment fails the mismatch density filter or if the basecall is ambiguous. |
| ConservativeGenotypeQuality | The model-based ConservativeGenotypeQuality (GQX) value for one sample, reflecting the conservative confidence of the called genotype. |
| NormalizedAltHaplotypeCountRatio | For variants in an active region, the proportion of reads supporting the top 2 haplotypes, or 0 if haplotyping failed due to this proportion being below threshold. For heterozygous variants with only one non-reference allele, the proportion is doubled so that its value is expected to be close to 1.0 regardless of genotype. The feature is set to −1 for variants not in an active region. |
| SampleIndelRepeatCount | The number of times the primary indel allele's repeat unit occurs in a haplotype containing the indel allele. The primary indel allele's repeat unit is the smallest possible sequence such that the inserted/deleted sequence can be formed by concatenating multiple copies of it. The primary indel allele is the best supported allele among all overlapping indel alleles at the locus of interest in one sample. |
| SampleIndelRepeatUnitSize | Length of the primary indel allele's repeat unit, as defined for feature SampleIndelRepeatCount. |
| SampleIndelAlleleBiasLower | The negative log probability of seeing N or fewer observations of one allele in a heterozygous variant out of the total observations from both alleles in one sample. N is typically the observation count of the reference allele. If the heterozygous variant does not include the reference allele, the first indel allele is used instead. |

-continued

| | |
|---|---|
| SampleIndelAlleleBias | Similar to SampleIndelAlleleBiasLower, except the count used is twice the count of the least frequently observed allele. |
| SampleProxyRMSMappingQuality | RMS mapping quality of all reads spanning the position immediately preceding the indel in one sample. This feature approximates the SAMPLE/MQ value defined in the VCF spec. |
| SamplePrimaryAltAlleleDepthFraction | The ratio of the confident observation count of the best-supported non-reference allele at the variant locus, over all confident allele observation counts in one sample. |
| ContextCompressability | The length of the upstream or downstream reference context (whichever is greater) that can be represented using 5 Ziv-Lempel keywords. The Ziv-Lempel keywords are obtained using the scheme of Ziv and Lempel 1977, by traversing the sequence and successively selecting the shortest subsequence that has not yet been encountered. |
| IndelCategory | A binary variable set to 1 if the indel allele is a primitive deletion or 0 otherwise. |
| SamplePrimaryAltAlleleDepth | The confident observation count of the best-supported non-reference allele at the variant locus. |
| VariantAlleleQuality | The model-based variant quality value reflecting confidence that the called variant is present in at least one sample, regardless of genotype. This feature matches QUAL in the VCF spec. |
| SampleMeanDistanceFromReadEdge | For all non-reference base call observations in one sample at a candidate SNV site, report the mean distance to the closest edge of each alternate base call's read. Distance is measured in read-coordinates, zero-indexed, and is allowed to have a maximum value of 20. |
| SampleRefAlleleDepth | The confident observation count of the reference allele at the variant locus. |
| SampleIndelMeanDistanceFromReadEdge | For all indel allele observations in one sample at a candidate indel locus, report the mean distance to the closest edge of each indel allele's read. Distance is measured in read-coordinates, zero-indexed, and is allowed to have a maximum value of 20. The left or right side of the indel may be used to provide the shortest distance, but the indel will only be considered in its left-aligned position. |
| SampleRefRepeatCount | The number of times the primary indel allele's repeat unit occurs in the reference sequence. |

Somatic Feature Descriptions:

Note that for somatic features "all samples" refers to the tumor and matched normal samples together.

| | |
|---|---|
| SomaticSNVQualityAndHomRefGermlineGenotype | Posterior probability of a somatic SNV conditioned on a homozygous reference germline genotype. When INFO/NT is "ref", this feature matches INFO/QSS_NT in the VCF output. |
| NormalSampleRelativeTotalLocusDepth | This feature matches the germline RelativeTotalLocusDepth feature, except that it reflects the depth of only the matched normal sample. |
| TumorSampleAltAlleleFraction | Fraction of the tumor sample's observations which are not the reference allele. This is restricted to a maximum of |

-continued

| | |
|---|---|
| | 0.5 to prevent the model from overtraining against high somatic allele frequencies (these might be common e.g. for loss of heterozygosity regions from liquid tumors). |
| RMSMappingQuality | Root mean square read mapping quality of all reads spanning the variant in all samples. This feature matches INFO/MQ in the VCF spec. |
| ZeroMappingQualityFraction | Fraction of read mapping qualities equal to zero, for all reads spanning the variant in all samples. |
| InterruptedHomopolymerLength | One less than the length of the longest interrupted homopolymer in the reference sequence containing the current position. An interrupted homopolymer is a string that has edit distance 1 to a homopolymer. |
| TumorSampleStrandBias | Log ratio of the tumor-sample somatic allele likelihood computed assuming the somatic allele occurs on only one strand vs both strands (thus higher values indicate greater bias). |
| TumorSampleReadPosRankSum | Z-score of Mann-Whitney U test for reference vs non-reference allele read positions in the tumor sample's observations. |
| AlleleCountLogOddsRatio | The log odds ratio of allele counts $\log \frac{r_t a_n}{r_n a_t}$, given reference $(r_t, r_n)$ and non-reference $(a_t, a_n)$ allele counts for the tumor and normal sample pair. |
| NormalSampleFilteredDepthFraction | The fraction of reads that were filtered out of the normal sample before calling the variant locus. |
| TumorSampleFilteredDepthFraction | The fraction of reads that were filtered out of the tumor sample before calling the variant locus. |
| SomaticIndelQualityAndHomRefGermlineGenotype | Posterior probability of a somatic indel conditioned on a homozygous reference germline genotype. When INFO/NT is "ref", this feature matches INFO/QSI_NT in the VCF output. |
| TumorSampleLogSymmetricStrandOddsRatio | Log of the symmetric strand odds ratio of allele counts $\log \left( \frac{r_{fwd} a_{rev}}{r_{rev} a_{fwd}} + \frac{r_{rev} a_{fwd}}{r_{fwd} a_{rev}} \right)$, given reference $(r_{fwd}, r_{rev})$ and non-reference $(a_{fwd}, a_{rev})$ confident counts of the tumor sample's observations. |
| RepeatUnitLength | The length of the somatic indel allele's repeat unit. The repeat unit is the smallest possible sequence such that the inserted/deleted sequence can be formed by concatenating multiple copies of it. |
| IndelRepeatCount | The number of times the somatic indel allele's repeat unit occurs in a haplotype containing the indel allele. |
| RefRepeatCount | The number of times the somatic indel allele's repeat unit occurs in the reference sequence. |
| TumorSampleIndelNoiseLogOdds | Log ratio of the frequency of the candidate indel vs all other indels at the same locus in the tumor sample. The frequencies are computed from reads which confidently support a single allele at the locus. |
| TumorNormalIndelAlleleLogOdds | Log ratio of the frequency of the candidate indel in the tumor vs normal samples. The frequencies are computed from reads which confidently support a single allele at the locus. |
| SiteFilteredBasecallFrac | The maximum value over all samples of SampleSiteFilteredBasecallFrac, which is the fraction of base calls at a site which have been removed by the |

-continued

| | |
|---|---|
| | mismatch density filter in a given sample. |
| IndelWindowFilteredBasecallFrac | The maximum value over all samples of SampleIndelWindowFilteredBasecallFrac, which is the fraction of base calls in a window extending 50 bases to each side of the candidate indel's call position which have been removed by the mismatch density filter in a given sample. |
| SpanningDeletionFraction | The maximum value over all samples of SampleSpanningDeletionFraction, which is the fraction of reads crossing a candidate SNV site with spanning deletions in a given sample. |

In some implementations, the input includes only EVS features. In other implementations, in the input, the EVS features can be supplemented by read data, as discussed above with the CNN implementations.

FIG. 1B illustrates one implementation of training the variant classifier of FIG. 1A using labeled training data comprising candidate variants (SNPs and indels). The variant classifier is trained on fifty thousand (50000) to one million (1000000) candidate variants (SNPs and indels) in various implementations. The candidate variants are labeled with true variant classifications and thus serve as the ground truth during the training. In one implementation, one million training examples of candidate variant sites with 50 to 100 reads each can be trained on a single GPU card in less than 10 hours with good recall and precision over 5-10 epochs of training. Training data can include NA129878 samples, with validation data from chromosome 2/20 held out. The variant classifier convolutional neural network is trained using backpropagation-based stochastic gradient descent algorithms such as Adam and regularization techniques like Dropout.

FIG. 1C depicts one implementation of input and output modules of convolutional neural network processing of the variant classifier of FIG. 1A. The input module includes feed the array of input features to the convolutional neural network, as discussed above. The output module includes translating analysis by the convolutional neural network into classification scores for likelihood that each candidate variant at the target base position is a true variant or a false variant. A final softmax classification layer of the convolutional neural network can produce normalized probabilities for the two classes that add up to unity (1). In the illustrated example, the softmax probability of the true positive (or true variant) is 0.85 and the softmax probability of the false positive (or false variant) is 0.15. Consequently, the candidate variant at the target base position is classified as a true variant.

For additional information about the architecture, training, inference, analysis, and translation of the variant classifier convolutional neural network, reference can be made to J. Wu, "Introduction to Convolutional Neural Networks," Nanjing University, 2017; I. J. Goodfellow, D. Warde-Farley, M. Mirza, A. Courville, and Y. Bengio, "CONVOLUTIONAL NETWORKS", Deep Learning, MIT Press, 2016; and "BATCH NORMALIZATION: ACCELERATING DEEP NETWORK TRAINING BY REDUCING INTERNAL COVARIATE SHIFT," arXiv: 1502.03167, 2015, which are incorporated by reference as if fully set forth herein.

In yet other implementations, the convolutional neural network of the variant classifier of FIG. 1A can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

Experimental Results

Figure 5:
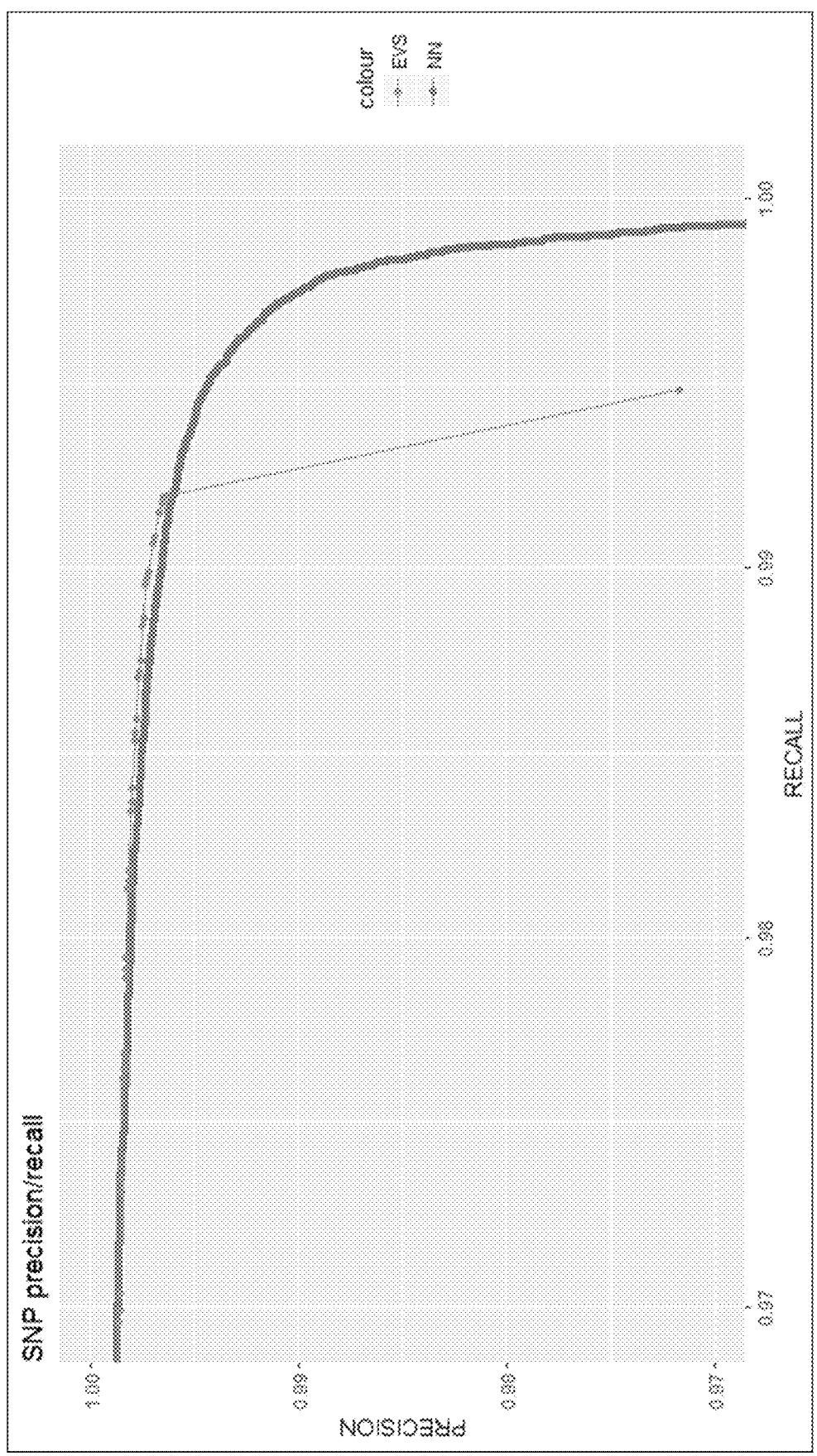
FIG. 5 shows one example of precision-recall curves that compare single-base polymorphism (SNP) classification performance by the convolutional neural network of the variant classifier and by a baseline Strelka™ model called empirical variant score (EVS) model.

FIG. 5 shows one example of precision-recall curves that compare single-base polymorphism (SNP) classification performance by the convolutional neural network of the variant classifier and by a baseline Strelka™ model called empirical variant score (EVS) model. As shown in FIG. 5, the convolutional neural network of the variant classifier has better precision-recall for SNPs than the EVS model.

Figure 6:
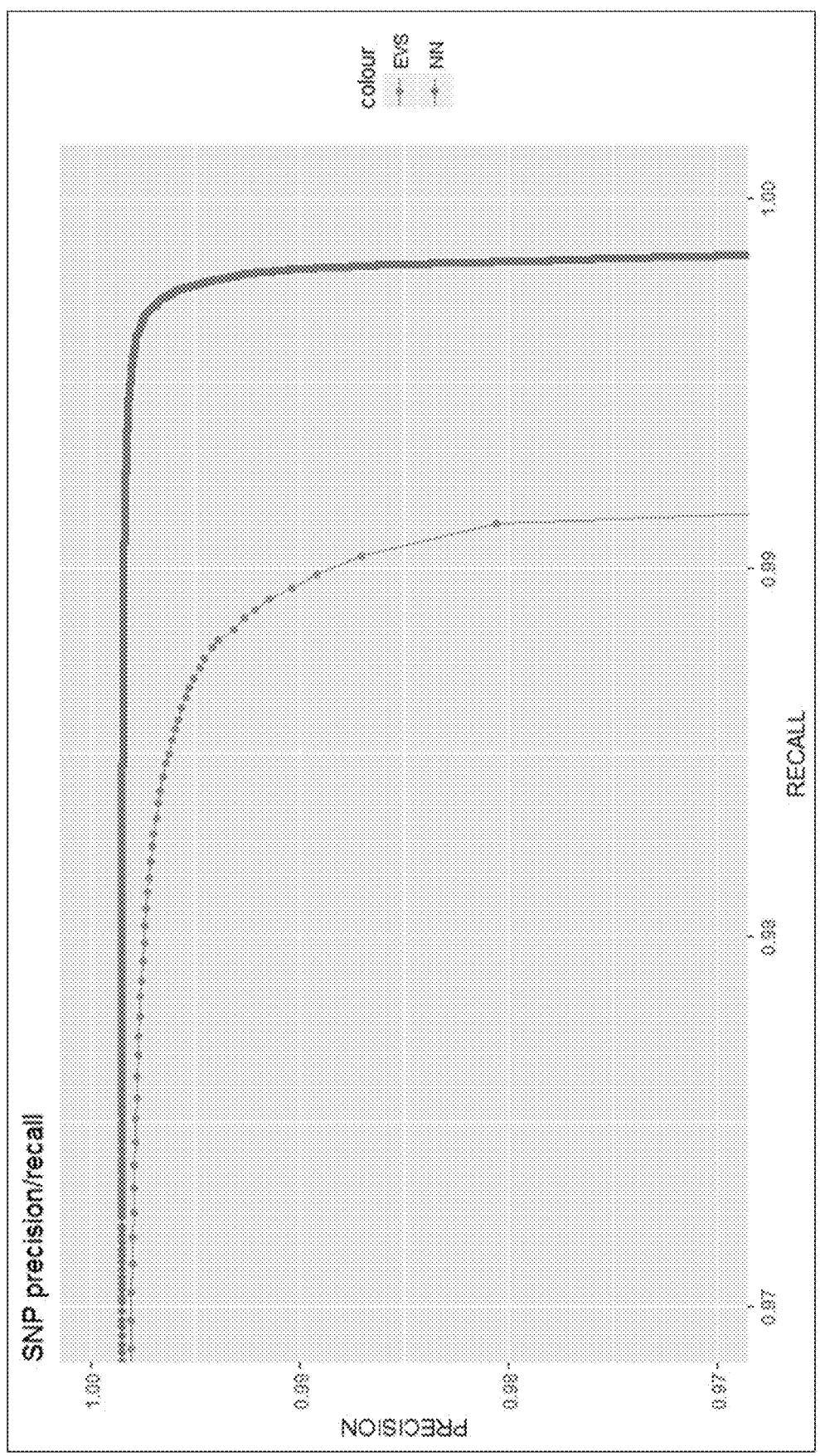
FIG. 6 shows another example of precision-recall curves that compare SNP classification performance by the convolutional neural network of the variant classifier and by the EVS model.

FIG. 6 shows another example of precision-recall curves that compare SNP classification performance by the convolutional neural network of the variant classifier and by the EVS model. Here, the convolutional neural network of the variant classifier is trained on a larger training set and thus further outperforms the EVS model.

Figure 7:
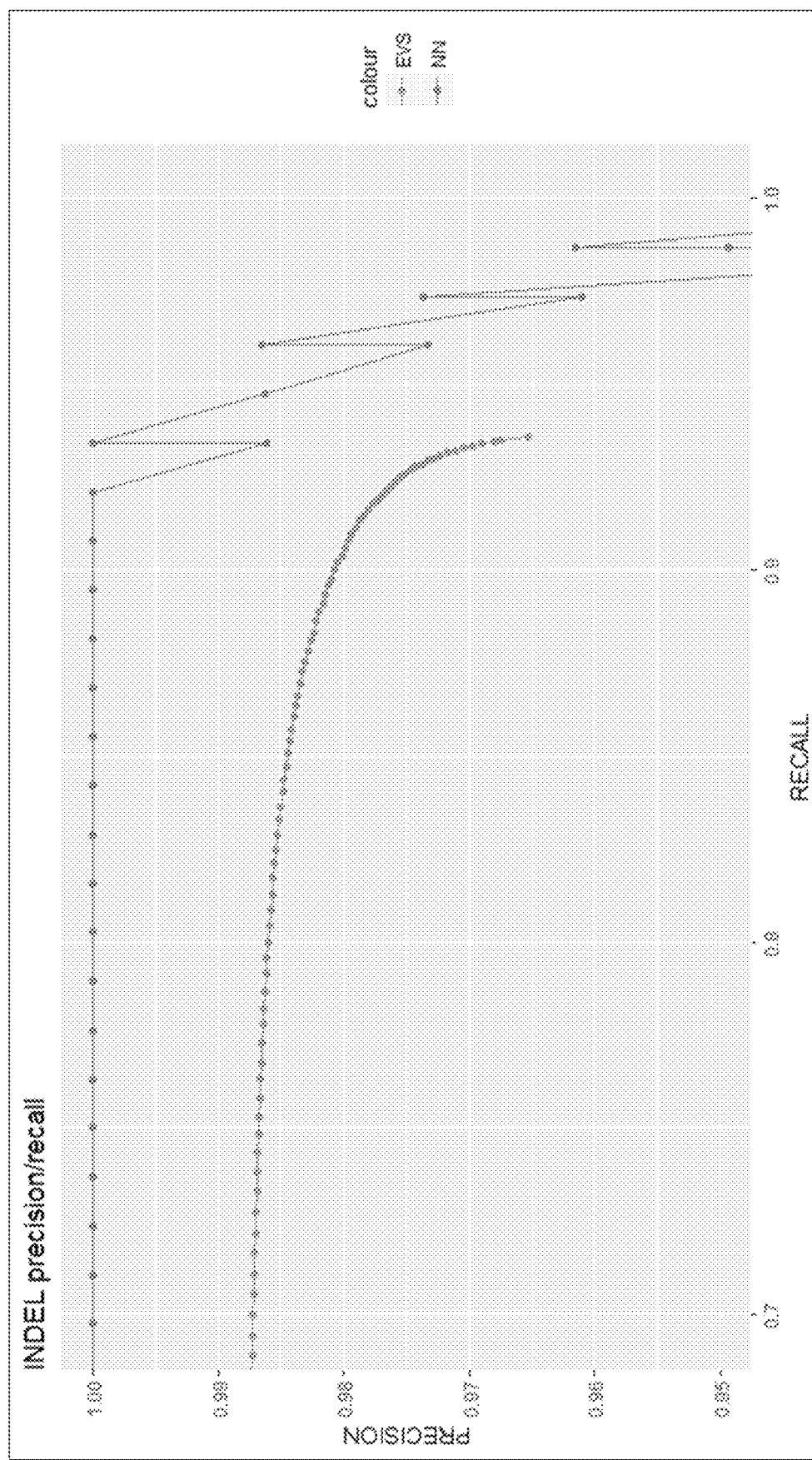
FIG. 7 depicts one example of precision-recall curves that compare indel classification performance by the convolutional neural network of the variant classifier and by the EVS model.

FIG. 7 depicts one example of precision-recall curves that compare indel classification performance by the convolutional neural network of the variant classifier and by the EVS model. As shown in FIG. 7, the convolutional neural network of the variant classifier has better precision-recall for indels than the EVS model.

Figure 8:
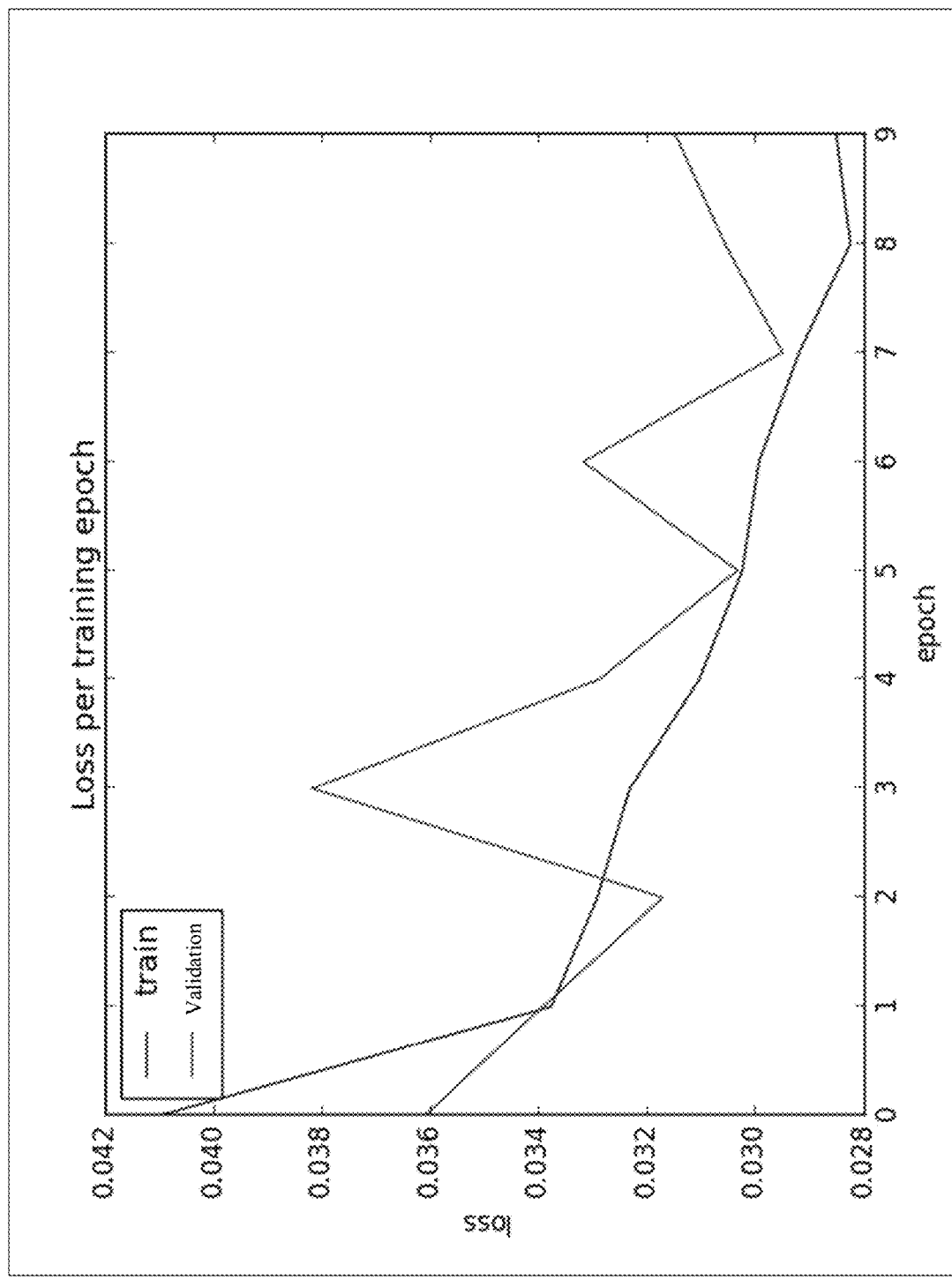
FIG. 8 illustrates convergence curves of the variant classifier during training and validation.

FIG. 8 illustrates convergence curves of the convolutional neural network of the variant classifier during training and validation. As shown in FIG. 8, the convolutional neural network converges around 8-9 epochs during training and validation, with each epoch taking around one hour to complete on a single GPU.

Figure 9:
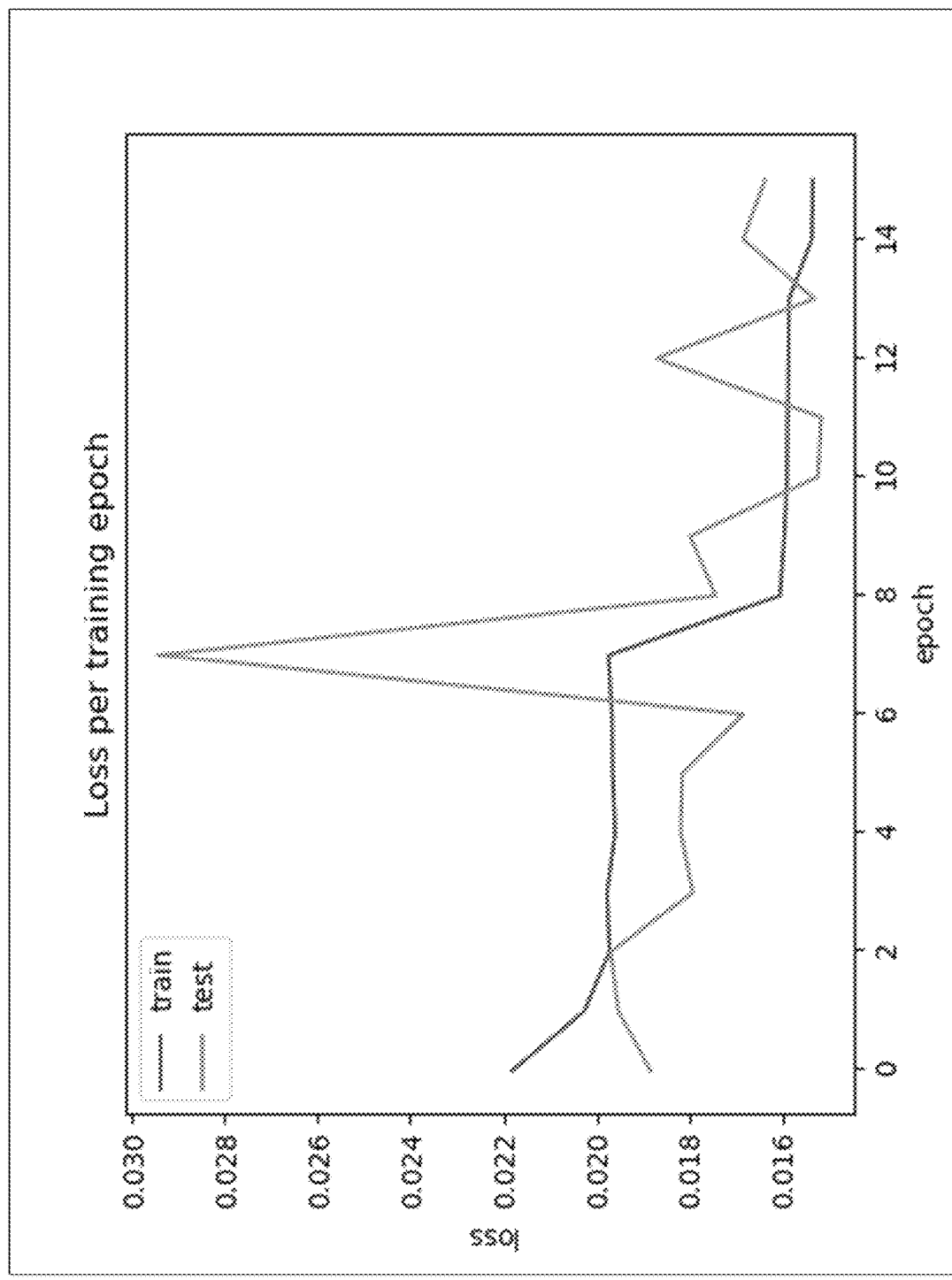
FIG. 9 illustrates convergence curves of the fully-connected neural network of the variant classifier during training and testing (inference).

FIG. 9 illustrates convergence curves of the fully-connected neural network of the variant classifier during training and testing (inference). As shown in FIG. 9, the fully-connected neural network converges after 14 epochs during training and testing.

In other implementations, the variant classifier can be trained for 50 epochs, with small improvements after 20 to 30 epochs without overfitting.

Figure 10:
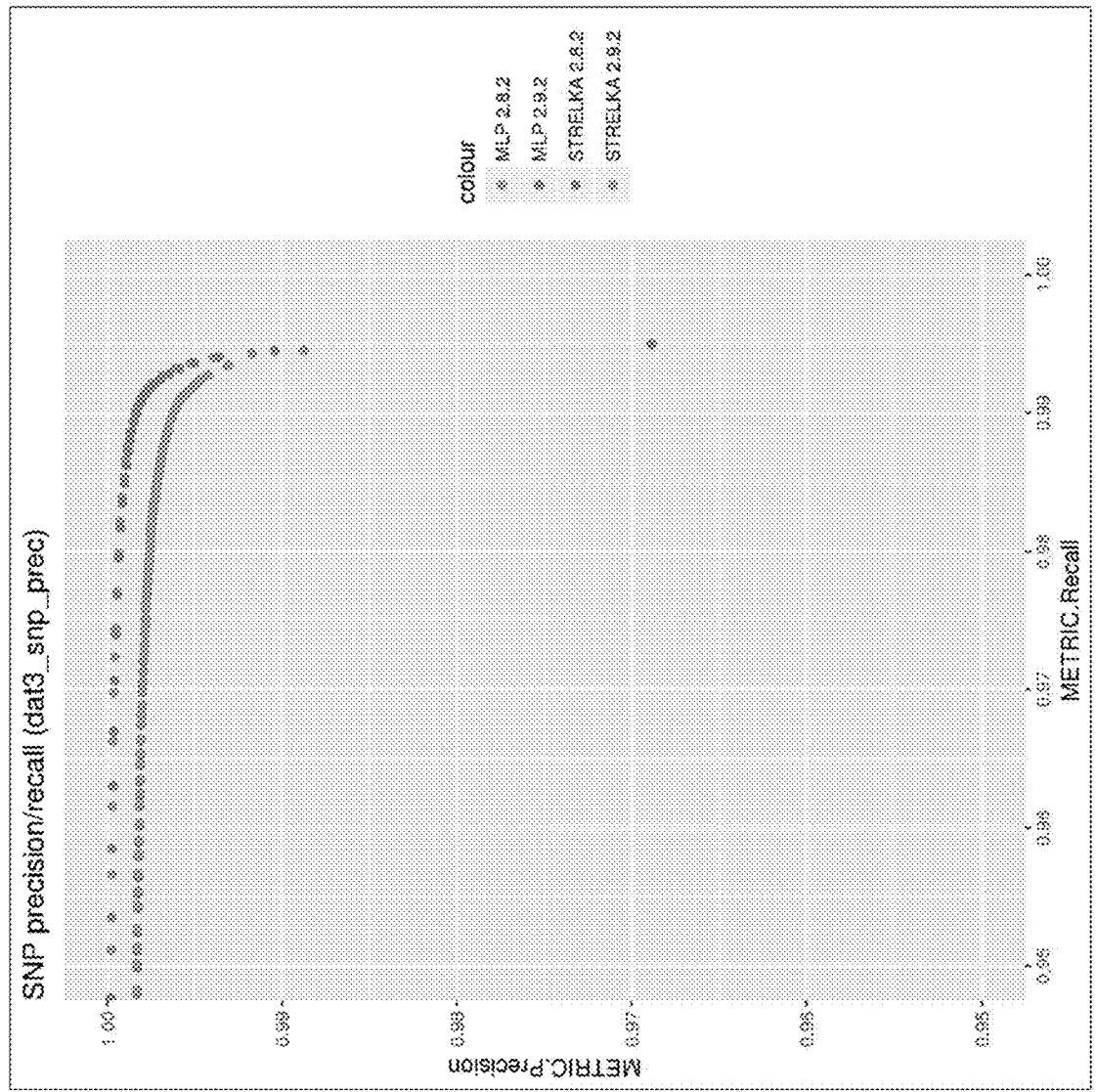
FIG. 10 uses precision-recall curves to compare SNP classification performance of (i) the fully-connected neural network of the variant classifier trained on EVS features of the EVS model version 2.8.2, (ii) the fully-connected neural network of the variant classifier trained on EVS features of the EVS model version 2.9.2, (iii) the EVS model version 2.8.2, and (iv) the EVS model version 2.9.2.

FIG. 10 uses precision-recall curves to compare SNP classification performance of (i) the fully-connected neural network of the variant classifier trained on EVS features of the EVS model version 2.8.2, (ii) the fully-connected neural network of the variant classifier trained on EVS features of the EVS model version 2.9.2, (iii) the EVS model version 2.8.2, and (iv) the EVS model version 2.9.2. As shown in FIG. 10, the fully-connected neural networks of the variant classifier outperform the EVS models.

Figure 11:
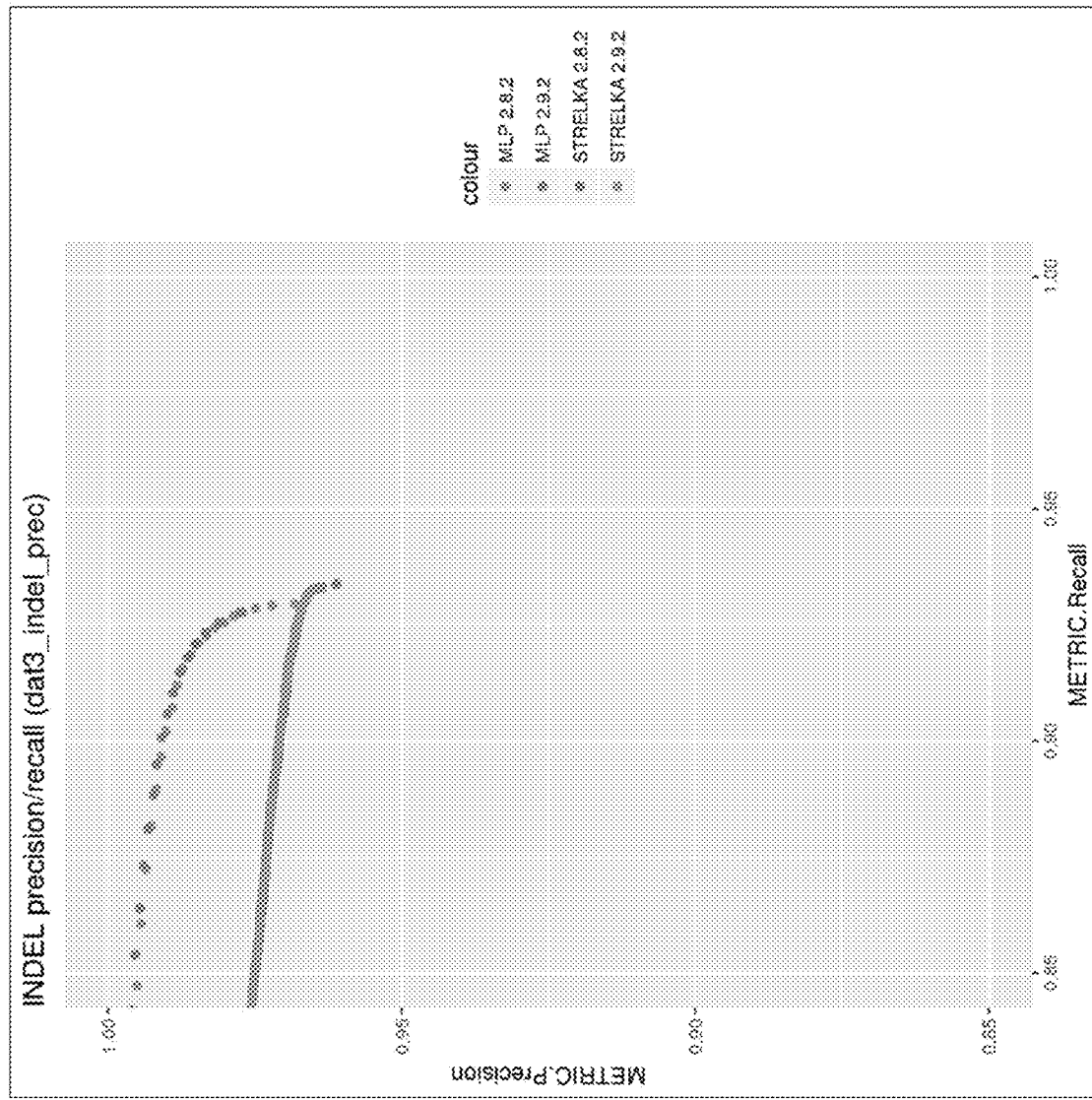
FIG. 11 uses precision-recall curves to compare indel classification performance of (i) the fully-connected neural network of the variant classifier trained on EVS features of the EVS model version 2.8.2, (ii) the fully-connected neural network of the variant classifier trained on EVS features of the EVS model version 2.9.2, (iii) the EVS model version 2.8.2, and (iv) the EVS model version 2.9.2.

FIG. 11 uses precision-recall curves to compare indel classification performance of (i) the fully-connected neural network of the variant classifier trained on EVS features of the EVS model version 2.8.2, (ii) the fully-connected neural network of the variant classifier trained on EVS features of the EVS model version 2.9.2, (iii) the EVS model version 2.8.2, and (iv) the EVS model version 2.9.2. As shown in FIG. 11, the fully-connected neural networks of the variant classifier outperform the EVS models.

Computer System

Figure 12:
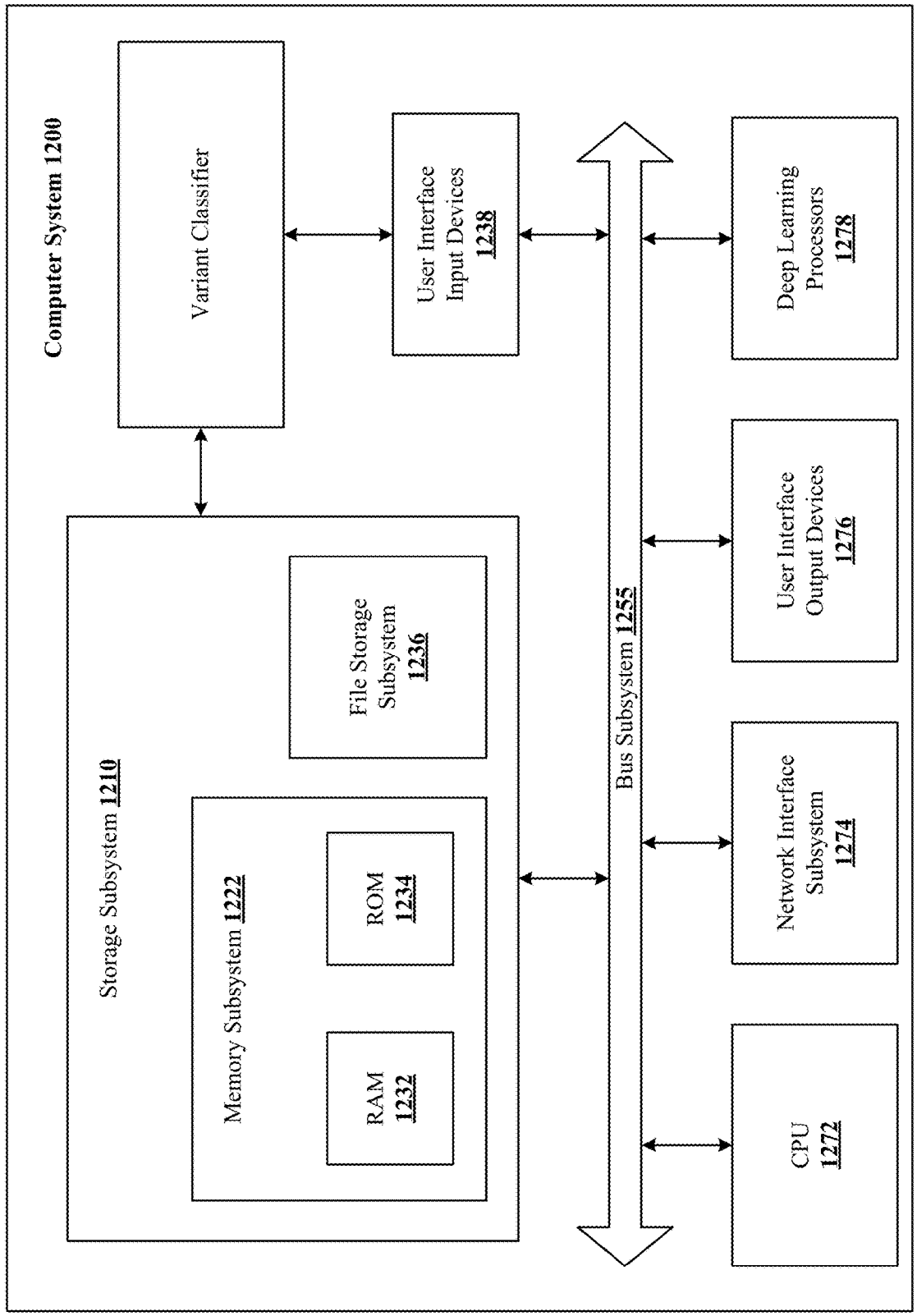
FIG. 12 is a simplified block diagram of a computer system that can be used to implement the variant classifier.

FIG. 12 is a simplified block diagram of a computer system that can be used to implement the variant classifier. Computer system 1200 includes at least one central processing unit (CPU) 1272 that communicates with a number of peripheral devices via bus subsystem 1255. These peripheral devices can include a storage subsystem 1210 including, for example, memory devices and a file storage subsystem 1236, user interface input devices 1238, user interface output devices 1276, and a network interface subsystem 1274. The input and output devices allow user interaction with computer system 1200. Network interface subsystem 1274 provides an interface to outside networks, including an interface to corresponding interface devices in other computer systems.

In one implementation, the variant classifier is communicably linked to the storage subsystem 1210 and the user interface input devices 1238.

User interface input devices 1238 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 1200.

User interface output devices 1276 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 1200 to the user or to another machine or computer system.

Storage subsystem 1210 stores programming and data constructs that provide the functionality of some or all of the modules and methods described herein. These software modules are generally executed by deep learning processors 1278.

Deep learning processors 1278 can be graphics processing units (GPUs), field-programmable gate arrays (FPGAs), application-specific integrated circuits (ASICs), and/or coarse-grained reconfigurable architectures (CGRAs). Deep learning processors 1278 can be hosted by a deep learning cloud platform such as Google Cloud Platform™, Xilinx™, and Cirrascale™. Examples of deep learning processors 1278 include Google's Tensor Processing Unit (TPU)™, rackmount solutions like GX4 Rackmount Series™, GX12 Rackmount Series™ NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™ NVIDIA's DRIVE PX™, NVIDIA's JETSON TX1/TX2 MODULE™, Intel's Nirvana™ Movidius VPU™, Fujitsu DPI™, ARM's DynamicIQ™, IBM TrueNorth™, and others.

Memory subsystem 1222 used in the storage subsystem 1210 can include a number of memories including a main random access memory (RAM) 1232 for storage of instructions and data during program execution and a read only memory (ROM) 1234 in which fixed instructions are stored. A file storage subsystem 1236 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 1236 in the storage subsystem 1210, or in other machines accessible by the processor.

Bus subsystem 1255 provides a mechanism for letting the various components and subsystems of computer system 1200 communicate with each other as intended. Although bus subsystem 1255 is shown schematically as a single bus, alternative implementations of the bus subsystem can use multiple busses.

Computer system 1200 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 1200 depicted in FIG. 12 is intended only as a specific example for purposes of illustrating the preferred embodiments of the present invention. Many other configurations of computer system 1200 are possible having more or less components than the computer system depicted in FIG. 12.

Particular Implementations

Convolutional Neural Network (CNN) Implementations

The technology disclosed relates to a system comprising a trained variant classifier. The variant classifier includes numerous processors operating in parallel and coupled to memory. The variant classifier also includes a convolutional neural network that runs on the numerous processors.

The convolutional neural network is trained on at least 50000 to 1000000 training examples of groups of reads that span candidate variant sites and are labeled with true variant classifications of the groups. Each of the training examples used in the training includes a group of reads that are aligned to a reference read. Each of the reads includes a target base position that is flanked by or padded to at least 110 bases on each side. Each of the bases in the reads is accompanied by a corresponding reference base in the reference read, a base call accuracy score of reading the base, a strandedness (i.e., DNA strandedness) of reading the base, insertion count of changes adjoining a position of the base, and deletion flag at the position of the base.

An input module of the convolutional neural network, which runs on at least one of the numerous processors, feeds the group of reads for evaluation of the target base position.

An output module of the convolutional neural network, which runs on at least one of the numerous processors, translates analysis by the convolutional neural network into classification scores for likelihood that each candidate variant at the target base position is a true variant or a false variant.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The convolutional neural network can have one or more convolution layers and one or more fully-connected layers. The convolutional neural network can process the group of reads through the convolution layers and concatenate output of the convolution layers with corresponding empirical variant score (abbreviated EVS) features. The convolutional neural network can further feed the result of the concatenation to the fully-connected layers.

The bases in the reads can be encoded using one-hot encoding. The corresponding base in the reference read can be encoded using one-hot encoding. The base call accuracy score of reading the base can be encoded as a continuous number. The strandedness of reading the base can be encoded using one-hot encoding. The insertion count of changes adjoining the position of the base can be encoded as a number. The deletion flag at the position of the base can be encoded as a number.

The candidate variant can be a candidate single-base polymorphism (abbreviated SNP). The candidate variant can be a candidate insertion or deletion (abbreviated indel).

The numerous processors can be part of a graphics processing unit (abbreviate GPU). The convolutional neural network can run on the GPU and iterate evaluation of the training examples over five to ten epochs, with one epoch taking one hour to complete. In other implementations, the variant classifier can be trained for 50 epochs, with small improvements after 20 to 30 epochs without overfitting In some implementations, the target base position can be flanked by or padded to at least 30 bases on each side.

The convolutional neural network can also have one or more max pooling layers and one or more batch normalization layers.

In some implementations, the convolutional neural network can be trained on one or more training servers. After the training, the convolutional neural network can be deployed on one or more production servers (supporting a cloud environment) that receive the group of reads from requesting clients. The production servers can process the group of reads through the input and output modules of the convolutional neural network to produce the classification scores that are transmitted to the clients.

Other implementations may include a non-transitory computer readable storage medium storing instructions executable by a processor to perform functions of the system described above.

In another implementation, the technology disclosed relates to a method of variant calling. The method includes feeding an array of input features to a convolutional neural network and processing the array through the convolutional neural network.

The array encodes a group of reads that are aligned to a reference read and include a target base position flanked by or padded to at least 30 bases on each side. Each input feature in the array corresponds to a base in the reads and has a plurality of dimensions.

The plurality of dimensions includes a first dimension set identifying the base, a second dimension set identifying a reference base aligned to the base, a third dimension set identifying a base call accuracy score of the base, a fourth dimension set identifying strandedness (e.g., DNA strandedness) of the base, a fifth dimension set identifying an insertion count of changes adjoining a position of the base, and a sixth dimension set identifying a deletion flag at the position of the base.

The method further includes translating processing of the array by the convolutional neural network into classification scores for likelihood that each input feature at the target base position is a true variant or a false variant.

In some implementations, each input feature can have twelve dimensions. In some implementations, the first dimension set can encode four bases using one-hot encoding. In some implementations, the second dimension set can encode four bases using one-hot encoding.

Each of the features discussed in this particular implementation section for the system implementations apply equally to this method implementation. As indicated above, all the system features are not repeated here and should be considered repeated by reference.

Other implementations may include a non-transitory computer readable storage medium storing instructions executable by a processor to perform the method described above. Yet another implementation may include a system including memory and one or more processors operable to execute instructions, stored in the memory, to perform the method described above.

In another implementation, the technology disclosed relates to a system comprising a trained variant classifier. The variant classifier includes numerous processors operating in parallel and coupled to memory. The variant classifier also includes a convolutional neural network that runs on the numerous processors.

The convolutional neural network is trained on at least 50000 to 1000000 training examples of groups of reads spanning candidate variant sites labeled with true variant classifications of the groups using a backpropagation-based gradient update technique that progressively matches outputs of the convolutional neural network with corresponding ground truth labels.

Each of the training examples used in the training includes a group of reads that are aligned to a reference read. Each of the reads includes a target base position that is flanked by or padded to at least 110 bases on each side.

Each of the bases in the reads is accompanied by a corresponding reference base in the reference read, a base call accuracy score of reading the base, a strandedness (i.e., DNA strandedness) of reading the base, insertion count of changes adjoining a position of the base, and deletion flag at the position of the base.

An input module of the convolutional neural network, which runs on at least one of the numerous processors, feeds the group of reads for evaluation of the target base position.

An output module of the convolutional neural network, which runs on at least one of the numerous processors, translates analysis by the convolutional neural network into classification scores for likelihood that each candidate variant at the target base position is a true variant or a false variant.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

Each of the bases in the reads can be further accompanied by a mapping quality score of aligning a corresponding read that contains the base to the reference read.

The convolutional neural network can have one or more convolution layers and one or more fully-connected layers. The convolutional neural network can process the group of reads through the convolution layers and concatenate output of the convolution layers with corresponding empirical variant score (abbreviated EVS) features, and feed the result of the concatenation to the fully-connected layers.

Each convolution layer has convolution filters and each of the convolution filters has convolution kernels. The convolution filters can use depthwise separable convolutions.

The convolutional neural network can have one or more max pooling layers and one or more batch normalization layers.

The convolutional neural network can use a softmax classification layer to produce the classification scores.

The convolutional neural network can use dropout.

The convolutional neural network can use flattening layers.

The convolutional neural network can use concatenation layers.

The convolutional neural network can run on a GPU and iterate evaluation of the training examples over five to fifty epochs, with one epoch taking one hour to complete.

Other implementations may include a non-transitory computer readable storage medium storing instructions executable by a processor to perform functions of the system described above.

In another implementation, the technology disclosed relates to a method of variant calling. The method includes feeding an array of input features to a convolutional neural network and processing the array through the convolutional neural network.

The convolutional neural network runs on numerous processors operating in parallel and coupled to memory, and is trained on at least 50000 training examples of groups of reads spanning candidate variant sites labeled with true variant classifications of the groups using a backpropagation-based gradient update technique that progressively matches outputs of the convolutional neural network with corresponding ground truth labels.

The array encodes a group of reads that are aligned to a reference read and include a target base position flanked by or padded to at least 30 bases on each side. Each input feature in the array corresponds to a base in the reads and has a plurality of dimensions.

The plurality of dimensions includes a first dimension set identifying the base, a second dimension set identifying a reference base aligned to the base, a third dimension set identifying a base call accuracy score of the base, a fourth dimension set identifying strandedness (e.g., DNA strandedness) of the base, a fifth dimension set identifying an insertion count of changes adjoining a position of the base, and a sixth dimension set identifying a deletion flag at the position of the base.

The method further includes translating processing of the array by the convolutional neural network into classification scores for likelihood that each input feature at the target base position is a true variant or a false variant.

Each of the features discussed in this particular implementation section for the system implementations apply equally to this method implementation. As indicated above, all the system features are not repeated here and should be considered repeated by reference.

Other implementations may include a non-transitory computer readable storage medium storing instructions executable by a processor to perform the method described above. Yet another implementation may include a system including memory and one or more processors operable to execute instructions, stored in the memory, to perform the method described above.

Fully-Connected Network (FCN) Implementations

In yet another implementation, the technology disclosed relates to a system comprising a trained variant classifier. The variant classifier includes numerous processors operating in parallel and coupled to memory. The variant classifier also includes a fully-connected neural network that runs on the numerous processors.

The fully-connected neural network is trained on at least 50000 to 1000000 training examples of empirical variant score (abbreviated EVS) feature sets of candidate variant sites labeled with true variant classifications of the site using a backpropagation-based gradient update technique that progressively matches outputs of the fully-connected neural network with corresponding ground truth labels.

Each of the training examples used in the training includes an EVS feature set representing characteristics of a corresponding candidate variant site in a group of reads.

An input module of the fully-connected neural network, which runs on at least one of the numerous processors, feeds the EVS feature set for evaluation of a target candidate variant site.

An output module of the fully-connected neural network, which runs on at least one of the numerous processors, translates analysis by the fully-connected neural network into classification scores for likelihood that at least one variant occurring at the target candidate variant site is a true variant or a false variant.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The fully-connected neural network can have one or more max pooling layers and one or more batch normalization layers.

The fully-connected neural network can use dropout.

The fully-connected neural network can use a softmax classification layer to produce the classification scores.

Other implementations may include a non-transitory computer readable storage medium storing instructions executable by a processor to perform functions of the system described above.

In another implementation, the technology disclosed relates to a method of variant calling. The method includes feeding an empirical variant score (abbreviated EVS) feature set of a target candidate variant site to a fully-connected neural network and processing the EVS feature set through the fully-connected neural network.

The fully-connected neural network runs on numerous processors operating in parallel and coupled to memory, and is trained on at least 50000 training examples of EVS feature sets of candidate variant sites labeled with true variant classifications of the site using a backpropagation-based gradient update technique that progressively matches outputs of the fully-connected neural network with corresponding ground truth labels.

The EVS feature set represents characteristics of the target candidate variant site.

The method further includes translating processing of the EVS feature set by the fully-connected neural network into classification scores for likelihood that at least one variant occurring at the target candidate variant site is a true variant or a false variant.

Each of the features discussed in this particular implementation section for the system implementations apply equally to this method implementation. As indicated above, all the system features are not repeated here and should be considered repeated by reference.

Other implementations may include a non-transitory computer readable storage medium storing instructions executable by a processor to perform the method described above. Yet another implementation may include a system including memory and one or more processors operable to execute instructions, stored in the memory, to perform the method described above.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

What is claimed is:

1. A system comprising:
at least one processor; and
a non-transitory computer readable medium storing a convolutional neural network and instructions that, when executed by the at least one processor, cause the system to:
identify a group of reads aligned with a reference genome and spanning a candidate variant at a target base position;
provide, to the convolutional neural network, an array of input features generated from a text file comprising sequencing data output by a sequencer instrument, the array of input features encoding:
bases from the group of reads in the text file at the target base position,
bases flanking each side of the target base position in the text file, and
corresponding base features for bases within the group of reads; and
generate, based on an analysis of the array of input features by the convolutional neural network, classification scores indicating likelihoods that the candidate variant at the target base position is a variant.

2. The system of claim 1, further comprising instructions that, when executed by the at least one processor, cause the system to generate the classification scores by generating a first probability that the candidate variant is a true variant and a second probability that the candidate variant is a false variant.

3. The system of claim 1, further comprising instructions that, when executed by the at least one processor, cause the system to generate the classification scores by generating one or more of a first score that the candidate variant is a homozygous variant, a second score that the candidate variant is a heterozygous variant, a third score that the candidate variant is a non-variant, or a fourth score that the candidate variant is a complex-variant.

4. The system of claim 1, further comprising instructions that, when executed by the at least one processor, cause the system to:
process the array of input features through one or more layers of the convolutional neural network to generate convolutional output features;
concatenate the convolutional output features with per-variant characterization data corresponding to the candidate variant at the target base position to generate concatenated features; and
generate the classification scores based on an analysis of the concatenated features by one or more layers of the convolutional neural network.

5. The system of claim 4, wherein the per-variant characterization data corresponding to the candidate variant comprise empirical variant score (EVS) features for the candidate variant.

6. The system of claim 4, further comprising instructions that, when executed by the at least one processor, cause the system to generate the classification scores based on the analysis of the concatenated features by one or more fully connected layers and a classification layer of the convolutional neural network.

7. The system of claim 4, further comprising instructions that, when executed by the at least one processor, cause the system to process the array of input features through the one or more layers of the convolutional neural network by processing the array of input features through a one or more of an input layer, a convolution layer, a batch normalization layer, a max pooling layer, or a flattening layer.

8. The system of claim 1, further comprising instructions that, when executed by the at least one processor, cause the system to provide the array of input features in which each feature corresponds to a base in a read from the group of reads and each feature comprises a plurality of dimensions.

9. The system of claim 1, wherein the corresponding base features for bases within the group of reads comprise one or more of:
a corresponding reference base in a reference read corresponding to the reference genome;
a base call accuracy score of calling a base in a read of the group of reads;
a strandedness of calling the base;
an insertion count of changes adjoining a position of the base;

a deletion flag at the position of the base; or a mapping quality score of aligning a corresponding read that contains the base to the reference read.

10. The system of claim 1, wherein the text file comprises a binary alignment map (BAM) file.

11. A non-transitory computer readable storage medium storing instructions that, when executed by at least one processor, cause a computing system to:

identify a group of reads aligned with a reference genome and spanning a candidate variant at a target base position;

provide, to a convolutional neural network, an array of input features generated from a text file comprising sequencing data output by a sequencer instrument, the array of input features encoding:
bases from the group of reads in the text file at the target base position,
bases flanking each side of the target base position in the text file, and
corresponding base features for bases within the group of reads; and generate, based on an analysis of the array of input features by the convolutional neural network, classification scores indicating likelihoods that the candidate variant at the target base position is a variant.

12. The non-transitory computer readable storage medium of claim 11, further storing instructions that, when executed by the at least one processor, cause the computing system to generate the classification scores by generating a first probability that the candidate variant is a true variant and a second probability that the candidate variant is a false variant.

13. The non-transitory computer readable storage medium of claim 11, further storing instructions that, when executed by the at least one processor, cause the computing system to generate the classification scores by generating one or more of a first score that the candidate variant is a homozygous variant, a second score that the candidate variant is a heterozygous variant, a third score that the candidate variant is a non-variant, or a fourth score that the candidate variant is a complex-variant.

14. The non-transitory computer readable storage medium of claim 11, further storing instructions that, when executed by the at least one processor, cause the computing system to:

process the array of input features through one or more layers of the convolutional neural network to generate convolutional output features;

concatenate the convolutional output features with per-variant characterization data corresponding to the candidate variant at the target base position to generate concatenated features; and generate the classification scores based on an analysis of the concatenated features by one or more layers of the convolutional neural network.

15. The non-transitory computer readable storage medium of claim 14, wherein the per-variant characterization data corresponding to the candidate variant comprise empirical variant score (EVS) features for the candidate variant.

16. The non-transitory computer readable storage medium of claim 14, further storing instructions that, when executed by the at least one processor, cause the computing system to generate the classification scores based on the analysis of the concatenated features by one or more fully connected layers and a classification layer of the convolutional neural network.

17. A computer-implemented method comprising:

identifying a group of reads aligned with a reference genome and spanning a candidate variant at a target base position;

providing, to a convolutional neural network, an array of input features generated from a text file comprising sequencing data output by a sequencer instrument, the array of input features encoding:
bases from the group of reads in the text file at the target base position,
bases flanking each side of the target base position in the text file, and
corresponding base features for bases within the group of reads; and generating, based on an analysis of the array of input features by the convolutional neural network, classification scores indicating likelihoods that the candidate variant at the target base position is a variant.

18. The computer-implemented method of claim 17, wherein generating the classification scores comprises generating a first probability that the candidate variant is a true variant and a second probability that the candidate variant is a false variant.

19. The computer-implemented method of claim 17, wherein generating the classification scores comprises generating one or more of a first score that the candidate variant is a homozygous variant, a second score that the candidate variant is a heterozygous variant, a third score that the candidate variant is a non-variant, or a fourth score that the candidate variant is a complex-variant.

20. The computer-implemented method of claim 17, wherein the corresponding base features for bases within the group of reads comprise one or more of:

a corresponding reference base in a reference read corresponding to the reference genome;

a base call accuracy score of calling a base in a read of the group of reads;

a strandedness of calling the base;

an insertion count of changes adjoining a position of the base;

a deletion flag at the position of the base; or a mapping quality score of aligning a corresponding read that contains the base to the reference read.

\* \* \* \* \*